United States Patent
Lee

(10) Patent No.: US 12,262,906 B2
(45) Date of Patent: Apr. 1, 2025

(54) ACUTE DELIVERY OF A DRUG OR FLUID TO AN OCULAR SURFACE

(71) Applicant: JLSP LLC, Wilmington, DE (US)

(72) Inventor: James H. Lee, Colorado Springs, CO (US)

(73) Assignee: JLSP LLC, Wilmington, DE (US)

( * ) Notice: Subject to any disclaimer, the term of this patent is extended or adjusted under 35 U.S.C. 154(b) by 828 days.

(21) Appl. No.: 17/606,599

(22) PCT Filed: Apr. 30, 2020

(86) PCT No.: PCT/US2020/030735
§ 371 (c)(1),
(2) Date: Oct. 26, 2021

(87) PCT Pub. No.: WO2020/223491
PCT Pub. Date: Nov. 5, 2020

(65) Prior Publication Data
US 2022/0296224 A1    Sep. 22, 2022

Related U.S. Application Data

(60) Provisional application No. 62/841,415, filed on May 1, 2019.

(51) Int. Cl.
*A61F 9/00* (2006.01)
*A61B 17/30* (2006.01)
*A61F 13/38* (2006.01)
*A61M 35/00* (2006.01)

(52) U.S. Cl.
CPC ............ *A61B 17/30* (2013.01); *A61F 9/0008* (2013.01); *A61M 35/006* (2013.01)

(58) Field of Classification Search
CPC ...... A61F 9/0008; A61F 9/0017; A61F 13/36; A61F 13/38; A61M 35/006
See application file for complete search history.

(56) References Cited

U.S. PATENT DOCUMENTS

| | | | | |
|---|---|---|---|---|
| 977,825 | A | * | 12/1910 | Murphy .................. A61F 13/38 604/1 |
| 1,256,831 | A | * | 2/1918 | Rogers ............. A61B 17/00234 604/1 |
| 3,595,241 | A | * | 7/1971 | Sheridan ........... A61M 25/0068 27/24.1 |

(Continued)

FOREIGN PATENT DOCUMENTS

| DE | 202004008544 U1 | 10/2004 |
|---|---|---|
| EP | 2745818 A1 | 12/2013 |

OTHER PUBLICATIONS

European Search Report; European Patent Office; European Application No. 20798068.1-1122 / 3962573; May 9, 2023; 7 pages.

(Continued)

*Primary Examiner* — Catharine L Anderson
(74) *Attorney, Agent, or Firm* — Taft Stettinius & Hollister LLP

(57) ABSTRACT

A system, assembly, or method for the acute delivery of medications or fluids to a surface such as the eye includes a rod coupled to an absorbent material. The rod and the absorbent material may be advanced through a casing to be delivered to a patient's tissue.

20 Claims, 8 Drawing Sheets

(56) References Cited

U.S. PATENT DOCUMENTS

| | | | |
|---|---|---|---|
| 4,784,506 A * | 11/1988 | Koreska | A61M 35/006 |
| | | | 401/133 |
| 4,957,385 A | 9/1990 | Weinstein | |
| 5,176,700 A | 1/1993 | Brown et al. | |
| 5,295,952 A | 3/1994 | Pietrafitta | |
| 6,152,923 A | 11/2000 | Ryan | |
| 6,467,982 B1 | 10/2002 | Tsao | |
| 2005/0011789 A1 | 1/2005 | Tsaur | |
| 2010/0286637 A1 | 11/2010 | Cable, Jr. et al. | |
| 2014/0088529 A1 | 3/2014 | Bengtson | |
| 2014/0249509 A1 | 9/2014 | Rubinfeld et al. | |
| 2014/0358124 A1 | 12/2014 | Glasser et al. | |

OTHER PUBLICATIONS

United States Patent & Trademark Office, The International Search Report and The Written Opinion Issued in corresponding International application No. PCT/US2020/030735, dated Jul. 14, 2020, 17 pp.

* cited by examiner

ACUTE DELIVERY OF A DRUG OR FLUID TO AN OCULAR SURFACE

This application is a national stage application of International Application No. PCT/US2020/030735, filed Apr. 30, 2020, which claims priority to and takes the benefit of U.S. Provisional Patent Application No. 62/841,415 filed on May 1, 2019, the contents of which are herein incorporated by reference.

RELATED APPLICATIONS

This application claims priority to U.S. Provisional Application No. 62/841,415, filed May 1, 2019, which is hereby incorporated by reference in its entirety.

FIELD OF THE INVENTION

The present invention relates generally to systems, assemblies, and methods for the acute delivery of medications or fluids to a surface such as the eye, and more particularly to a system, assembly, or method for the delivery of medications or fluids to the eye.

BACKGROUND OF THE INVENTION

Glaucoma is a group of eye conditions often caused by an abnormally high pressure in the eye that can damage the optic nerve. Traditionally, glaucoma may be managed by eye drops, laser trabeculoplasty, bleb-forming surgery, and/or minimally invasive glaucoma surgery (MIGS). With some types of MIGS, a surgeon may insert an injector through a patient's cornea and through the sclera at or anterior to Schlemm's canal to position a distal end of a stent within a subconjunctival space of the eye. This creates a pathway for aqueous to flow from an anterior chamber to the subconjunctival space of the eye, forming a bleb. A drug such as Mitomycin C may be injected into the subconjunctival space to prevent scar formation and bleb failure.

Mitomycin C inhibits DNA synthesis, halts cell replication, and eventually cause cell death; therefore, the precision and accuracy of Mitomycin C placement is vital to the maintained health of the eye. The amount of Mitomycin C applied to a tissue is also vital. Therefore, what is needed is an improved system and method for application of a drug or agent, such as Mitomycin C to tissue of the eye. More generally, an improved system, assembly, and method is needed for delivery of a drug or agent to tissue of the body.

SUMMARY OF THE INVENTION

The disclosure relates generally to a system and a method for the acute delivery of medications or fluids to a surface such as the eye, and more particularly to a system or method for the delivery of medications or fluids to the eye in connection with surgical procedures. The disclosure provides for various methods to be used to provide acute drug administration to a surface utilizing a simple applicator wherein the applicator comprises an absorbent material attached to the distal end of a thin rod wherein a cylindrical plastic casing can be operably retracted and extended allowing the absorbent material to either be extended beyond the distal end of the cylindrical casing or covered by the casing.

In an illustrative embodiment, the method comprises: i) applying the drug to the absorbent material which attached to a thin rod where the thin rod can be covered by an outer cylindrical casing which can be retracted allowing the absorbent material to extend beyond the distal end of outer casing; ii) subsequently retracting the rod such that the absorbent material filled with drug is retracted into the cylindrical plastic casing; iii) the apparatus can then be lowered into position to where the drug is to be applied; then iv) being able to retract the cylindrical casing such that the absorbent material is placed into contact with the surface for a sufficient amount of time to allow the drug to disperse onto the surface; v) extending the cylindrical plastic casing such that the absorbent material is covered, and then removing the entire apparatus.

In an illustrative embodiment, a method of acute drug administration to a surface utilizing a simple applicator wherein the applicator comprises: an absorbent material attached to the distal end of a thin rod wherein a cylindrical plastic casing can be operably retracted and extended allowing the absorbent material to either be extended beyond the distal end of the cylindrical casing or covered by the casing; the method comprising: i) applying the drug to the absorbent material wherein the thin rod is in a position such that the outer cylindrical casing is retracted allowing the absorbent material is extended beyond the distal end of the cylindrical plastic casing; ii) subsequently retracting the rod such that the absorbent material filled with drug is retracted into the cylindrical plastic casing; iii) lowering the apparatus into position to where the drug is to be applied; then iv) retracting the cylindrical casing such that the absorbent material is placed into contact with the surface for a sufficient amount of time to allow the drug to disperse onto the surface; v) extending the cylindrical plastic casing such that the absorbent material is covered, and then removing the entire apparatus. In some embodiments, the apparatus is disposable.

In some embodiments, the drug is administered immediately prior to a subsequent surgical or other procedure. In some embodiments, the absorbent material is sterilized prior to use.

In some embodiments, the absorbent material is selected from the group comprising a sponge, micro-sponge, nano-sponge, gelatin-foam, cellulose, cotton gauze, rayon, hydrogel, polyvinyl acetate, and polypropylene.

In some embodiments, the surface comprises an eye including the conjunctiva, sclera, cornea, pupil, iris, and eyelid. In some embodiments, the surface comprises an outer surface of the body selected from the skin, nail, and mucous membrane. In some embodiments, the drug is to be administered inside the body during a surgical or medical procedure.

In some embodiments, the absorbent material is about 1-5 mm in diameter. In some embodiments, the absorbent material is about 1-5 mm thick. In some embodiments, the absorbent material is allowed to come into contact with the desired surface for a sufficient amount of time to allow for the drug to exert its effects.

In another illustrative embodiment, a method of acute drug administration to a surface utilizing an applicator to deliver an absorbent material wherein the applicator delivers an absorbent material containing a drug, the method comprises: i) applying the drug to the absorbent material; ii) directing the apparatus into position to where the drug is to be applied; then iii) placing the absorbent material into contact with the surface for a sufficient amount of time to allow the drug to disperse onto the surface; iv) removing the absorbent the absorbent material from the surface. In some embodiments, the drug is administered immediately prior to a subsequent surgical or other procedure. In some embodiments, the apparatus is disposable.

In some embodiment, the absorbent material is selected from the group comprising a sponge, micro-sponge, nano-sponge, gelatin-foam, cellulose, cotton gauze, rayon, hydrogel, polyvinyl acetate, and polypropylene.

In some embodiments, the surface comprises an eye including the conjunctiva, sclera, cornea, pupil, iris, and eyelid. In some embodiments, the surface comprises an outer surface of the body selected from the skin, nail, and mucous membrane.

In some embodiments, the absorbent material is about 1-5 mm in diameter. In some embodiments, the absorbent material is about 1-5 mm thick. In some embodiments, the absorbent material is allowed to come into contact with the desired surface for a sufficient amount of time to allow for the drug to exert its effects.

The aspects of the disclosure provide the distinct advantages of currently available methods of acute drug delivery, particularly injection types of drug delivery, including: i) the ability to provide target specific drug delivery to a localized region or space; ii) the ability to adjust the specific time and exposure based on the concentration of the drug applied; iii) production of fewer drug and other surgical side effects, e.g. scarring, bleb formation, etc, and, iv) is disposable, sterile and cost effective.

In another illustrative embodiment, an applicator assembly for an eye includes: a hollow casing including a first end having a first opening defined therein and a second end having a second opening defined therein; a pincher rod positioned within the hollow casing, configured to slide relative to the casing, and including: a main body having: a top surface, a bottom surface, a central portion positioned between the top surface and the bottom surface, and a central axis extending through the central portion, a claw coupled to the main body and including a top jaw and a bottom jaw spaced apart and defining a first gap therebetween, wherein the central axis passes through the gap; and an absorbent material including a front end, a back end, and first and second edges extending between the front end and the back end; wherein the absorbent material is positioned in the first gap defined between the top jaw and the bottom jaw; and wherein the absorbent material is disposed in a compressed state when positioned in the first gap.

In some embodiments, absorbent material is selected from the group comprising a sponge, micro-sponge, nano-sponge, gelatin-foam, cellulose, cotton gauze, rayon, hydrogel, polyvinyl acetate, and polypropylene.

In some embodiments, the main body includes a first edge and a second edge extending between the top and bottom surfaces of the main body; and wherein the claw includes a top surface and a bottom surface; wherein the top jaw includes a first outer edge extending downward from the top surface of the claw on a first lateral side of the central axis and a second outer edge extending downward from the top surface of the claw on a second lateral side of the central axis; and wherein the first outer edge of the top jaw is flush with the first edge of the main body and the second outer edge of the top jaw is flush with the second edge of the main body.

In some embodiments, the top jaw includes a first arm and a second arm spaced laterally apart from the first arm to defined a second gap therebetween; and wherein the first outer edge of the top jaw is defined by the first arm, and the second outer edge of the top jaw is defined by the second arm. In some embodiments, the absorbent material is plus-sign-shaped; and a portion of the absorbent material is positioned in the second gap.

In some embodiments, the absorbent material is cuboid-shaped. In some embodiments, the main body includes a first edge and a second edge extending between the top and bottom surfaces of the main body; and the first edge of the absorbent material is flush with the first edge of the main body and the second edge of the absorbent material is flush with the second edge of the main body when the absorbent material is positioned in the first gap defined between the top jaw and the bottom jaw. In some embodiments, the claw includes a top surface and a bottom surface; the absorbent material includes a top surface and a bottom surface; and the top surface of the absorbent material is flush with the top surface of the claw and the bottom surface of the absorbent material is flush with the bottom surface of the claw when the absorbent material is positioned in the gap defined between the top jaw and the bottom jaw.

In some embodiments, the casing includes a top side and a bottom side; and the first opening is defined by a void in the bottom side. In some embodiments, the top side of the casing extends adjacent the first opening to a terminus defined in an end wall extending downward from the top side of the casing. In some embodiments, the end wall includes an inner surface facing toward the absorbent material; and the absorbent material is movable to a further compressed state when engaged with the end inner surface of the end wall.

In some embodiments, the hollow casing includes a retractable cover positioned at the first end of the hollow casing; and the retractable cover is moveable between: (i) a closed position in which the retractable cover blocks the first opening, and (ii) an open position in which the retractable cover does not block the first opening.

In another illustrative embodiment, applicator assembly for an eye comprises a hollow casing including a first end having a first opening defined therein and a second end having a second opening defined therein; a pincher rod positioned within the hollow casing, configured to slide relative to the hollow casing, and including: a main body having: a top surface, a bottom surface, a central portion positioned between the top surface and the bottom surface, and a central axis extending through the central portion, a claw coupled to the main body and including a top jaw and a bottom jaw spaced apart and defining a first gap therebetween, wherein the central axis passes through the gap; and an absorbent material including a front end, a back end, and first and second edges extending between the front end and the back end; wherein the absorbent material is positioned in the first gap defined between the top jaw and the bottom jaw; and wherein the absorbent material is disposed in a compressed state when positioned in the first gap.

In some embodiments, the hollow casing includes a retractable cover positioned at the first end of the casing; and the retractable cover is moveable between: (i) a closed position in which the retractable cover blocks the first opening, and (ii) an open position in which the retractable cover does not block the first opening.

In some embodiments, the hollow casing includes a top side and a bottom side; the first opening is defined by a void in the bottom side; and the first opening is further defined by an end wall extending downward from the top side of the hollow casing. In some embodiments, the end wall is u-shaped, having a first leg a second leg, and a terminus connecting the first and second legs; the absorbent material is configured to be disposed in a further compressed state when urged against the terminal portion of the end wall.

In another illustrative embodiment, a method of operating an applicator assembly includes: positioning an absorbent material in a compressed state between a top jaw and a bottom jaw of first claw coupled to a main body of a pincher rod; inserting the pincher rod into a hollow casing; advancing the pincher rod through the hollow casing toward an opening of the hollow casing; delivering a substance carried by the absorbent material to a patient's tissue; retracting the pincher rod through the hollow casing away from the opening.

In some embodiments, delivering the substance carried by the absorbent material to the patient's tissue includes: urging the absorbent material against an end wall defining a portion of the opening to compress the absorbent material beyond the compressed state.

In some embodiments, the method further comprises: moving the retractable cover from: a first position in which the retractable cover extends to the end wall to block delivery of the substance to the patient's tissue, to a second position in which the retractable cover is spaced apart from the end wall and does not block delivery of the substance to the patient's tissue. In some embodiments, the method further comprises: decoupling the first claw from the pincher rod; and coupling a second claw to the pincher rod.

In another illustrative embodiment, an applicator assembly comprises: a hollow casing including a first end having a first opening defined therein and a second end having a second opening defined therein; a shielding rod positioned within the hollow casing, configured to slide relative to the hollowing casing, and including: a top side and a bottom side opposite the top side; a distal end, a proximal end opposite the distal end, and a main body positioned between the distal end and the proximal end; a shield coupled to the main body and defined at the distal end of the shielding rod, the shield including a top portion coupled to extending distally away from the main body; and an absorbent material including a top surface and a bottom surface; wherein the absorbent material is coupled to the shielding rod and positioned below the top portion of the shield.

In some embodiments, the top portion of the shield is defined at the top side of the shielding rod. In some embodiments, the bottom surface of the absorbent material is positioned at the bottom side of the shielding rod when the absorbent material is coupled to the shielding rod. In some embodiments, the bottom surface of the absorbent material is flush with a bottom surface of the bottom side of the shielding rod when the absorbent material is coupled to the shielding rod. In some embodiments, the top of surface of the absorbent material is coupled to the top portion of the shield.

In some embodiments, the absorbent material is eclipsed by the top portion of the shield when the applicator assembly is viewed from a top down view. In some embodiments, the absorbent material is visible when the shielding rod is viewed from a bottom up view.

In some embodiments, the distal end of the shielding rod is formed to include a cavity defined in part by the top portion of the shield. The absorbent material is positioned in the cavity.

In some embodiments, the shield includes an end wall extending downward from the top portion of the shield and cooperating to define the cavity. In some embodiments, the end wall is a U-shaped end wall including a pair of legs and an inner surface positioned between the pair of legs; and the pair of legs are positioned between the inner surface of the end wall and the main body.

In some embodiments, the shield includes a bottom portion defined at the bottom side of the shielding rod; and the bottom portion is coupled to extends distally away from the main body. The bottom surface of the absorbent material partially is eclipsed by the bottom portion of the shield when the applicator assembly is viewed from a bottom up view.

In some embodiments, the bottom portion of the shield is retractable and extendable to expose more or less surface area of the bottom surface of the absorbent material.

In another illustrative embodiment, the applicator assembly comprises: a hollow casing including a first end having a first opening defined therein and a second end having a second opening defined therein; a shielding rod positioned within the hollow casing, configured to slide relative to the hollow casing, and including: a top side and a bottom side opposite the top side; a distal end, a proximal end opposite the distal end, and a main body positioned between the distal end and the proximal end; a shield removably coupled to the main body at the distal end of the shielding rod, the shield including a top portion; and an absorbent material including a top surface and a bottom surface; wherein the absorbent material is coupled to the shield and positioned below the top portion of the shield with the top surface facing the top portion of the shield.

In some embodiments, the top portion of the shield is aligned with the top side of the shielding rod when the shield is coupled to the shielding rod. In some embodiments, the shielding rod is formed to include a cavity defined in part by the top portion of the shield; and the absorbent material is positioned in the cavity.

In some embodiments, the shield includes an end wall extending downward from the top portion of the shield and cooperating to define the cavity. In some embodiments, the end wall is a U-shaped end wall including a pair of legs and an inner surface positioned between the pair of legs; and the pair of legs are positioned between the inner surface and the main body when the shield is coupled to the shielding rod.

In some embodiments, the shield includes a bottom portion aligned with the bottom side of the shielding rod when the shield is coupled to the shielding rod; and the bottom surface of the absorbent material faces the bottom portion of the shield when the absorbent material is positioned in the cavity.

In some embodiments, the bottom portion of the shield is coupled to the inner surface of the end wall; and the bottom portion of the shield the extends proximally away from the inner surface toward the main body when the shield is coupled to the shielding rod. In some embodiments, the bottom portion of the shield is spaced apart from the shielding rod when the shield is coupled to the shielding rod.

In some embodiments, the shield is a first shield; and the applicator assembly further comprises a second shield configured to be coupled to the shielding rod subsequent to the first shield being removed from the shielding rod.

In another illustrative embodiment, a method of operating an applicator assembly comprises: inserting a shielding rod having a first absorbent material coupled thereto into a hollow casing; advancing the shielding rod through the hollow casing toward an opening of the hollow casing; applying a substance carried by the first absorbent material to a first portion of patient's tissue; retracting the shielding rod through the hollow casing away from the opening.

In some embodiments, the first portion of patient's tissue is a target region to which the drug is to be applied; and applying a substance carried by the first absorbent material to a first portion of patient's tissue includes: contacting the target region with the first absorbent material, and contacting a non-targeted region, to which the substance is not to be applied, with a shield of the shielding rod positioned adjacent the first absorbent material.

In some embodiments, the method further comprises: repositioning the hollow casing; inserting the shielding rod into the hollow casing with a second absorbent material attached to the shielding rod; advancing the shielding rod through the hollow casing toward the opening of the hollow casing; applying a substance carried by the second absorbent material to a second portion of the patient's tissue; and retracting the shielding rod through the hollow casing away from the opening.

In some embodiments, the method further comprises: repositioning the hollow casing; inserting the shielding rod into the hollow casing with a third absorbent material attached to the shielding rod; advancing the shielding rod through the hollow casing toward the opening of the hollow casing; applying a substance carried by the third absorbent material to a third portion of the patient's tissue; and retracting the shielding rod through the hollow casing away from the opening.

In some embodiments, the method further comprises; forming a void in fibroblasts positioned in the subconjunctival space of the patient's tissue; marking the first portion of the patient's tissue to indicate a target region for the substance to be applied. In some embodiments, the target region is defined along a boundary of the void.

In some embodiments, the method further comprises: creating an incision in the eye of the patient. In some embodiments, repositioning the hollow casing includes pivoting the hollow casing at the incision to direct the opening of the hollow casing toward the second portion of the patient's tissue.

In some embodiments, the method further comprises: selecting a desired surface area of the first absorbent material to be exposed to the first portion of the patient's tissue based on at least the concentration of the substance and the time the first absorbent material is to be applied to the patient's tissue.

In some embodiments, the method further comprises: adjusting the surface area of the first absorbent material to be exposed to the first portion of the patient's tissue based on the desired surface area; wherein adjusting the surface area of the first absorbent material includes moving a bottom portion of the shield relative to a main body of the shielding rod.

In another illustrative embodiment, a method of operating an applicator assembly comprises: inserting a first shielding rod having a first absorbent material coupled thereto into a hollow casing; advancing the first shielding rod through the hollow casing toward an opening of the hollow casing; applying a substance carried by the first absorbent material to a first portion of patient's tissue; retracting the first shielding rod through the hollow casing away from the opening.

In some embodiments, the first portion of patient's tissue is a target region to which the drug is to be applied; and applying a substance carried by the first absorbent material to a first portion of patient's tissue includes: contacting the target region with the first absorbent material, and contacting a non-targeted region, to which the substance is not to be applied, with a shield of the shielding rod positioned adjacent the first absorbent material.

In some embodiments, the method further comprises: repositioning the hollow casing; inserting a second shielding rod into the hollow casing with a second absorbent material attached to the second shielding rod; advancing the second shielding rod through the hollow casing toward the opening of the hollow casing; applying a substance carried by the second absorbent material to a second portion of the patient's tissue; and retracting the second shielding rod through the hollow casing away from the opening.

In some embodiments, the method further comprises: creating an incision in the eye of the patient. In some embodiments, repositioning the hollow casing includes pivoting the hollow casing at the incision to direct the opening of the hollow casing toward the second portion of the patient's tissue.

In some embodiments, method further comprises: selecting a desired surface area of the first absorbent material to be exposed to the first portion of the patient's tissue based on at least the concentration of the substance and the time the absorbent material is to be applied to the patient's tissue.

In some embodiments, the method further comprises: adjusting the surface area of the first absorbent material to be exposed to the first portion of the patient's tissue based on the desired surface area; and adjusting the surface area of the first absorbent material to be exposed includes moving a bottom portion of the shield.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

Various other features and attendant advantages of the present invention will be more fully appreciated from the following detailed description when considered in connection with the accompanying drawings in which like reference characters designate like or corresponding parts throughout the several views, and wherein.

DETAILED DESCRIPTION

Figure 1:
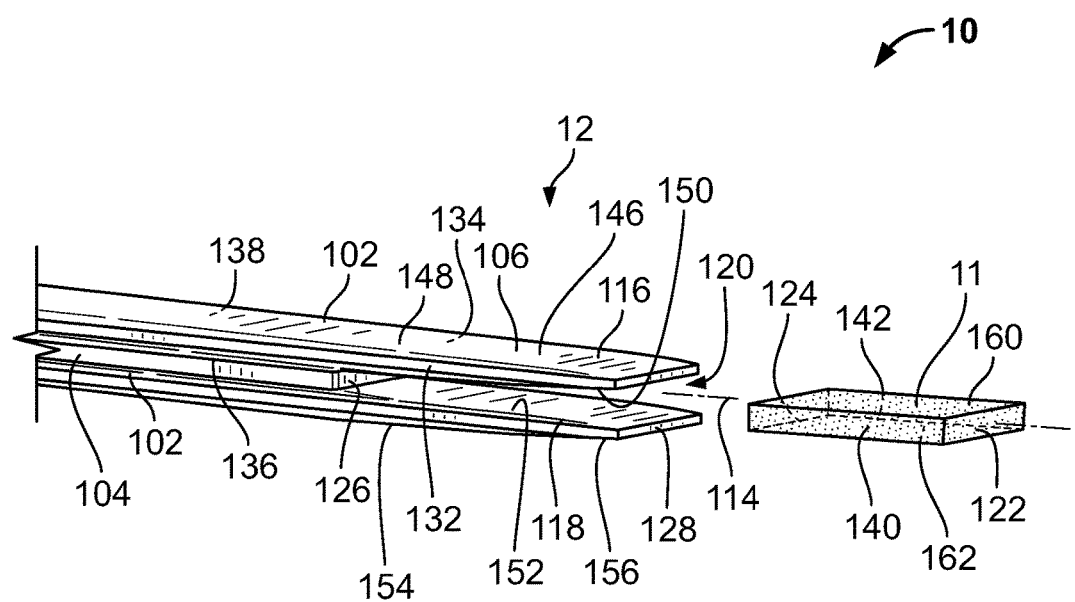
FIG. 1 is a perspective view of an apparatus, sometimes referred to as an applicator assembly, including a portion of a thin rod, sometimes referred to as a pincher rod, and an absorbent material positionable in a distal end of the pincher rod.

Referring now to the drawings generally, there is illustrated a schematic of the apparatus 10 disclosed in which absorbent material 11 is attached to the distal end of a thin rod 12 enclosed within the outer casing 13. Although the outer casing 13 is sometimes referred to as a cylindrical casing, it should be appreciated that the term cylindrical should not be interpreted to mean that each embodiment of the casing is a geometric cylinder.

As shown the absorbent material 11 is attached to the distal end of a thin rod 12 wherein the absorbent material 11 extends beyond the outer cylindrical plastic casing 13. It should be appreciated that the apparatus 10 can be operated to move the absorbent material 11 outside of the outer casing 13 in different ways. For example, either the outer casing 13 is fixed and the thin rod 12 can operably move in and out of the outer cylindrical plastic casing 13 or alternatively, the thin rod 12 can be fixed allowing the outer cylindrical casing 13 to operably move. It can be further appreciated that in either method of operation of the apparatus 10, the end result is the same (i.e. the absorbent material 11 is placed in contact with a tissue surface 50. The outer cylindrical casing 13 moving or the thin rod 12 moving, the absorbent material 11 is removable from the thin rod 12 or otherwise positionable in a container to allow drug to be absorbed by the absorbent material. The absorbent material 11, in a non-limiting example, is approximately 1 mm thick×3 mm square.

The thin rod 12 may be simply thrust into the absorbent material 11 when the absorbent material 11 is, for example, a sponge or sponge-like material. Alternatively, the end of the thin rod 12 may be equipped with a type of caliper or claw-like device to grab the absorbent material 11. The caliper or claw-like device to grab the absorbent material 11 may be used to place the absorbent material 11 onto or adjacent to the tissue surface 50. The absorbent material 11 can be left on the tissue for a sufficient length of time to allow the drug to diffuse or interact with the tissue surface 50. Following a sufficient length of time, the absorbent material 11 can be picked up or grabbed again by the caliper or claw-like device, retracted into the outer cylindrical casing 13 and then removed.

Figure 2:
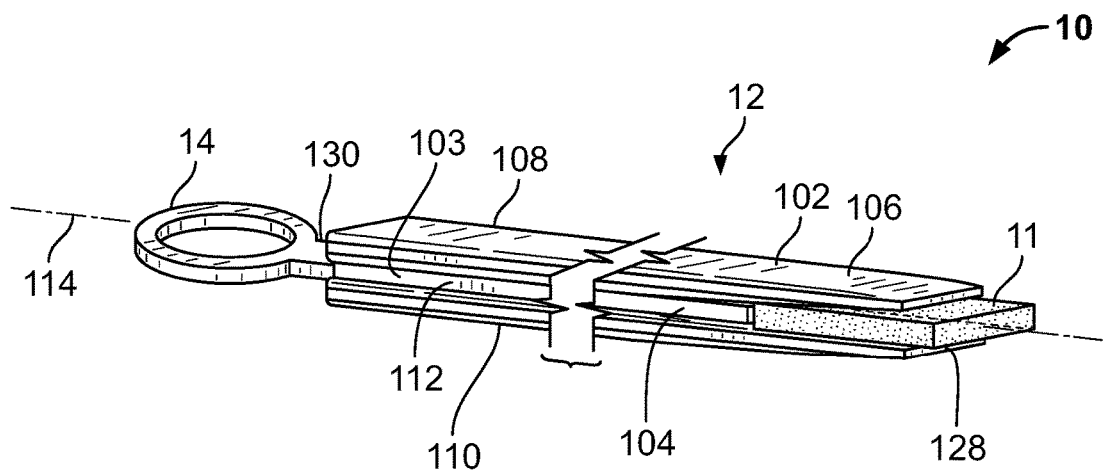
FIG. 2 is a side view of the absorbent material positioned in the pincher rod.

As shown in FIG. 2 apparatus 10 may include a finger loop 14 at the proximal end of the thin rod 12 which allows for ease of advancing the thin rod 12 through the outer cylindrical casing 13 to place the absorbent material 11 onto and/or in contact with the tissue surface 50.

Figure 9A:
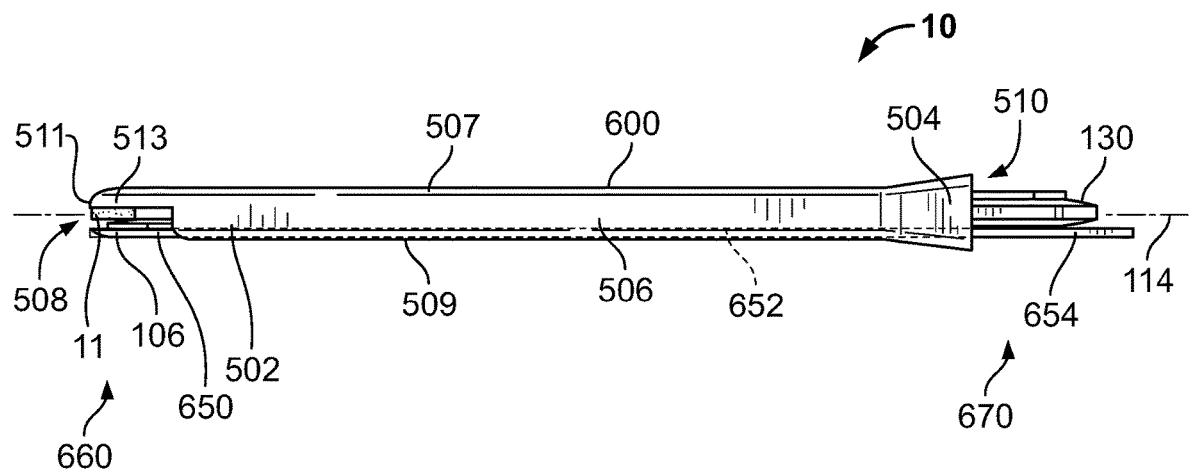
FIG. 9*a* is a side view of the absorbent material and the pincher rod of FIG. 2 and the hollow casing of FIG. 7, showing that the hollow casing may include a retractable cover shown in a closed position.
Figure 9B:
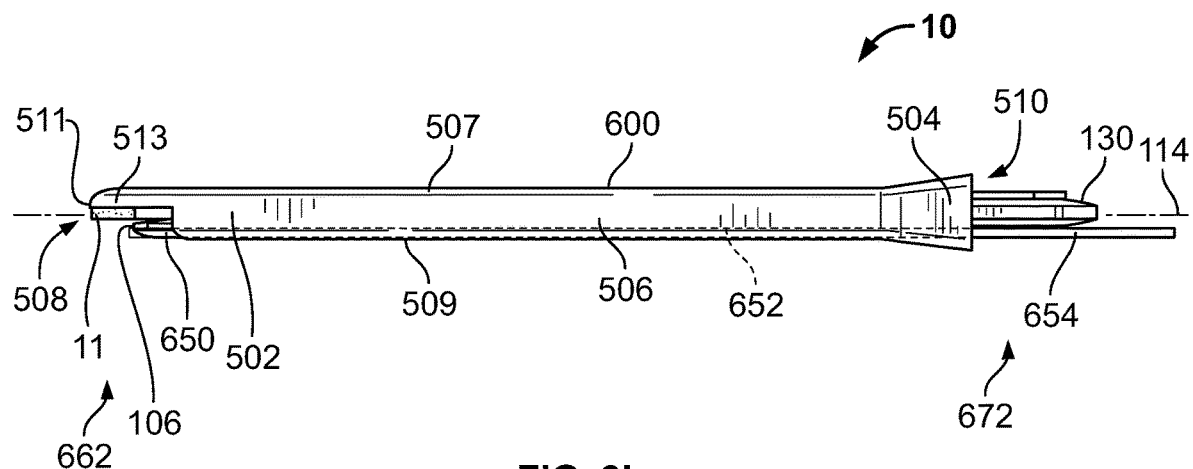
FIG. 9b is a side view of the components of FIG. 9a, showing the retractable cover in an open position.

As shown in FIGS. 9a-b, the outer casing 13 includes a retractable window 15 that can be opened or retracted (see FIG. 9b) to allow drug to be delivered onto the tissue surface 50 from the absorbent material 11 through the retractable window 15 where the drug simply diffuses from the absorbent material 11 but where the absorbent material 11 does not make contact with the tissue surface 50. The retractable window 15 will be oriented to face only one side depending upon what aspect of the tissue surface 50 the user wishes to target. The retractable window 15 may be referred to as a retractable cover 15a configured to extend over an aperture 15b. In some The aperture 15b opening to only one side of the applicator assembly 10 depending upon what aspect of the tissue surface 50 the user wishes to target.

In another variation, the absorbent material 11 can be pushed through the aperture 15b to allow the absorbent material 11 to come directly into contact with the tissue surface 50. In yet another variation, the retractable window 15 can be located direct at the distal end of the outer cylindrical casing 13.

In still yet another variation, the drug can be delivered onto the absorbent material 11 after the absorbent material has been placed onto the tissue surface 50.

With substantial modification, intraocular lens (IOL) injectors, may be operable with the apparatus 10. IOLs are key components of cataract surgery and are utilized to provide a lens to the eye during cataract surgery. Clear corneal incisions, microincisions, and foldable intraocular lenses (IOLs) allow ophthalmologists to perform minimally invasive cataract surgery, reducing the potential for astigmatism and optimizing visual quality in refractive lens exchange. These devices are utilized routinely to provide soft silicon or acrylic lenses and are either folded or rolled and are then injected with minimal manipulation and potential damage. In cataract surgery, utilizing IOLs allows small incisions, minimal inflammation, a low risk of early post-operative infection and faster would healing.

With such devices, absorbent material can be preloaded into the IOL delivery system. Such IOL devices have been routinely used to deliver ophthalmic visco-surgical devices (OVDs) via a capsular bag during IOL delivery to form enough space for IOL implantation.

As non-limiting examples, see Fabian ("Injector Systems for Foldable Intraocular Lens Implantation," in Kohnen, T (ed): *Modern Cataract Surgery. Dev Ophthalmol.* Basel, Karger, 2002, 34: pp 147-154, which is incorporated herein by reference), which provides a review of several types of IOLs by several different manufacturers that can be utilized with the apparatus 100.

Existing devices such as the XEN® Glaucoma Treatment System by Allergan, Inc. disclosed in at least U.S. Pat. Nos. 6,007,511; 8,663,303; 8,721,702; 8,765,210; 8,852,136; 8,852,256; 9,017,276; 9,192,516; 9,095,413; 9,113,994, 9,192,516; 9,877,866; and, 10,085,884 are stents or glaucoma implants designed to reduce intraocular pressure in eyes suffering from refractory glaucoma. According to the manufacturer, the device creates a permanent channel through the sclera allowing flow of aqueous humor from the anterior chamber into the subconjunctival space and is inserted using an injector through a small corneal incision. Bleb scar formation is commonly seen with chronic implants. A drug such as Mitomycin C may be injected into the subconjunctival space to prevent scar formation and bleb failure. Neither the XEN® nor any other MIGS device or procedure is indicated for acute drug delivery using a sponge-material or absorbent material 11 and/or the casing 13 disclosed herein.

The apparatus 10 can be used to deliver a variety of drugs or other substances that can be applied to the absorbent material 11. For example, Mitomycin C is an immunosuppressive antimitotic agent which that is utilized cataract and glaucoma surgery to prevent scarring by inhibiting the multiplication of cells which produce scar tissue. Mitomycin C has been shown to reduce the risk of surgical failure in cataract and glaucoma surgeries. The apparatus can be utilized to deliver Mitomycin C to the ocular surface. Other such agents include: cyclosporine, lifitegrast, interferon, 5-flurouracil.

Other drugs that can be used with the apparatus 10 including but not limited to: cholinergic agonists such as: acetylcholine, carbochol, pilocarpine; anticholinesterase agents such as echothiophate; muscarinic antagonists such as: atropine, scopolamine, homatropine, cyclopentolate, tropicamide; alpha-adrenergic agonists such as: phenylephrine, apraclonidine, brimonidine, naphazoline, tetrahydrozoline; beta-adrenergic antagonists such as: betaxolol, timolol, carteolol, levobunolol, metipranolol; prostaglandin analogues such as: latanoprost, travoprost, bimatoprost, tafluprost; carbonic anhydrase inhibitors such as: acetazolamide, methazolamide, dorzolamide, brinzolamide; anti-VEGF agents including: verteporfin, pegaptanib, bevacizumab, ranbizumab; anti-inflammatory agents such as: topical calcineurin inhibitors including cyclosporine, tacrilimus, pimecrolimus, voclosporin, polyunsaturated fatty acids, doxycycline, blood-derived eye drops derived from autologous serum, allogenic serum eyedrops, platelet-rich plasma eyedrops, umbilical cord autologous serum eyedrops, albumin eyedrops, secretogues such as pilocarpine hydrochloride, cevimeline, bethanechol, eledoisin, mucolytics such as bromhexine, ambroxol and N-acetylcysteine, anti-collagenolytics such as tetracycline, doxycycline, and minocycline; hormonal therapies, chemotherapeutic agents, antibiotics such as: azithromycin, besifloxacin, chloramphenicol, ciprofloxacin, fusidic acid, gatifloxacin, gentamicin, levofloxacin, lomefloxacin, moxifloxacin, neomycin-polymyxin B-gramcidin, netilimicin, norfloxacin, ofloxacin, povidone-iodine, rifamycin, tobramycin; antifungals such as azole derivatives including: econazole, clotrimazole, miconazole, itraconazole, fluconazole, bifonazole, ketoconazole, oxiconazole, voriconazole; antifungal polyene derivatives such as amphotericin B, natamycin; antivirals including nucleoside derivatives such as pyrimidine analogues including idoxuridine T, trifluridine T, brivudine U, sorivudine U; purine analogues including vidarabine A, valacyclovir G, acyclovir G, ganciclovir G, famiciclovir G, peniciclovir G, valganciclovir, cidofovir; non-nucleoside analogues such as cidofovir and foscarnet; antiallergy treatments such as antihistamines including naphazoline/pheniramine, levocabastine, emedastine; mast-cell stabilizers such as: cromolyn, nedocromil, lodoxamide, pemirolast, alcaftadine, azelastine, bepotastine, epinastine, ketotifen, olopatadine; glucocorticoids such as: dexamethasone, difluprednate, fluorometholone, loteprednol etabonate, prednisolone acetate, prednisolone sodium acetate, rimexolone, triamcinolone, betamethasone, fluocinolone acetonide, methylprednisolone, prednisone, prednisolone, desonide, dexamethasone; polymers, hydrogels, chondroitin sulfate, bioadhesives, and the like; vitamins, oils, monoclonal antibodies and other drugs and agents that a person of skill in the art would recognize as being beneficial to the eye. The apparatus 10, in some cases, may be used to apply a drug or agent to the eye prior to, during, or immediately after an ocular procedure or surgery.

The absorbent material 11 can be composed of any of a variety of materials known to those skilled in the art. For example, it is to be noted that the sponges may comprise sponges having different thickness dimensions, different sizes, and may be fabricated from different materials comprising different porosity characteristics so as to predetermine saturation volumes and retention times with respect to the fluids, drugs, or medications being delivered to necessary surface such as the eye. For example, differently-sized sponges can of course be used depending upon the size of the region of the eye being treated. Still further, the sponge can have a diametrical extent which is larger than that of the area to be treated per se.

It should also be readily apparent that nanosponges or microsponges can also be used as the absorbent material 11 of the current invention. See for example Patel et al., Int. J. Res. in Pharmacy Chem., 2012, 2(2): pp. 237-244. Nanosponges have an average diameter of 1 µm while microsponges are 10-25 microns in diameter. Nanosponges may be made of many different organic or inorganic including titanium or other metal-oxide based materials, silicon particles, carbon coated metallic, hyper-cross-linked polystyrene and, cyclodextrin. Microsponges typically are macroporous beads, usually 10-25 microns in diameter, loaded with a medication or fluid. Microsponges are porous, polymeric microspheres that are mostly used for prolonged topical administration but can be adapted for acute administration of medications or fluids as described herein. Microsponges are designed to deliver a pharmaceutically active ingredient efficiently at minimum dose and also to enhance stability, reduce side effects, and modify drug release profile.

Other types of absorbent material can include foams, hydrogels, polymers such as polypropylene, cellulose, sodium polycrylate, polycrylamide copolymer; plastic resins. Absorbent materials can also be composed of biological materials or composites of biological materials and polymers. For example, McKittrick et al, *Materials Science and Engineering* C 30 (2010); pp. 331-342, incorporated herein by reference, discloses that such materials similar to structural biological materials such as mollusk shells, diatoms, sea sponges, teeth, tusks, bone, antlers, crab exoskeletons and insect cuticles that are composites of a biopolymers, i.e. structural proteins such as collagen, keratin and elastin and polysaccharides such as cellulose and chitin, combined with a and a mineral phase such as calcium carbonate, carbonated hydroxy-apatite, or silica.

EXAMPLE

Use of the Acute Drug Delivery Device of the Present Invention During Deployment of an Intraocular Shunt Device The device and methods herein may be utilized to provide acute drug administration during various intraocular procedures included, but not limited to, the deployment of an intraocular shunt into an eye as disclosed in, for example, U.S. Pat. Nos. 6,007,511; 8,663,303; 8,721,702; 8,765,210; 8,852,136; 8,852,256; 9,017,276; 9,192,516; 9,095,413; 9,113,994, 9,192,516; 9,877,866; and, 10,085,884. The device and methods of the current invention have been utilized to deliver Mitomycin-c at various concentrations, for example 0.2 mg/ml-10 mg/ml depending on the tissue target into the subconjunctival space immediately prior to implantation of an intralocular shunt as described above. A 3 mm sponge soaked with Mitomycin-c was allowed to remain in situ for 30 sec to 120 sec.

The amount of time the sponge rests in place can be determined empirically based upon several factors including: drug concentration, patient factors such as but limited to, ethnicity, age, sex, previous medical history, previous cataract surgery, etc. Tissue exposure time can be adjusted to prevent bleb scar formation commonly seen with chronic implants such as with XEN® stents. Hohberger, B. et al., "MIGS [minimal invasive glaucoma surgery]: Therapeutic Success of Combined Xen Gel Stent Implantation with Cataract Surgery," *Graefe's Archive for Clinical and Experimental Ophthalmology* (2018) 256:621-625 discloses that therapeutic failure rate of 46.7%-49.4%. The present invention allows more localized and focal delivery of drug with higher success rates.

Appropriate post-operative follow-up demonstrated that the acute administration of mitomycin-c via the acute application of a sponge from a device of the current invention was able to minimize or prevent bleb scar formation around the tip of the intraocular shunt during the post-operative phase as shown in. When treated according to this method, the conjunctiva maintains its normal appearance unlike the white, avascular appearance seen when mitomycin-c drug is directly injected.

The applicator assembly 10 may be used in a variety of applications including in association with surgeries anywhere in a patient's body including, for example, the eye. The applicator assembly 10 may also be used, for example, in the context of, ophthalmology, urology, gastroenterology, neurology, cardiology, and the like.

Referring now to the drawings in a more detailed manner, several components of the applicator assembly 10 are illustrated in FIGS. 1 and 2. In particular, FIG. 1 illustrates the absorbent material 11 and a first side 102 of the pincher rod 12. FIG. 2 illustrates the pincher rod 12 coupled to the absorbent material 11. The pincher rod 12 includes a main body 104 extending from the first side 102 to a second side 103, a claw 106 defined at the first side 102, and a tab 130 defined at the second side 103. The main body 104 includes a top surface 108, a bottom surface 110, and a central portion 112 defined between the top surface 108 and the bottom surface 110. The main body 104 extends along a central axis 114 defined through the central portion 112 thereof. It should be appreciated that the top surface 108 is positioned above the central axis or on a first vertical side of the central axis 114, and the bottom surface 110 is positioned below the central axis 114 or on a second vertical side of the central axis.

As shown in FIG. 1, the claw 106 includes a top jaw 116 and a bottom jaw 118 each extending away from the main body 104 substantially parallel to the central axis 114. The top jaw 116 and the bottom jaw 118 are spaced apart in the vertically (as oriented in FIG. 1) to define a gap 120 therebetween. The central axis 114 extends through the gap 120. As shown in FIG. 2, the absorbent material 11 is positionable in the gap 120 such that the central axis 114 extends through the absorbent material 11 when the absorbent material 11 is coupled to the pincher rod 12. In some embodiments, the jaws 116, 118 are flexible such that the gap 120 may be expanded to position the absorbent material 11 therein. In some embodiments, the absorbent material 11 is compressible. In any event, the absorbent material is secured within the gap 120 as a result of a compressive force applied by the jaws 116, 118 to the absorbent material 11.

As shown in FIGS. 1 and 2, the absorbent material 11 includes a front end 122 and a back end 124. The back end 124 may abut and/or be positioned adjacent a back surface 126 of the claw 106 that is positioned between the top and bottom jaws 116, 118. Each jaw 116, 118 extends at least from the back surface 126 to a terminus 128 of the claw 106. As shown in FIG. 2, in some embodiments, the front end 122 of the absorbent material 11 extends beyond the terminus 128 of the claw 106.

As shown in FIG. 2, the tab 130 may be coupled to the finger loop 14. In some embodiments, the tab 130 extends to form the finger loop 14 such that the tab 130 and the finger loop 14 are a single monolithic component. In other words, the finger loop 14 may comprise the tab 130. In some embodiments, the tab 130 is a first component extending from the main body 104 and the finger loop 14 is otherwise coupled to the tab 103. In some embodiments, the finger loop 14 is a partial loop, otherwise known as a hooked or curved extension protruding from or formed with the tab 130.

As suggested by FIG. 1, the top and bottom jaws 116, 118 are oriented such that they are mirror images of one another and are otherwise substantially identical; therefore, any description of the top jaw 116 applies equally to the bottom jaw 118. The jaw 116 includes a first edge 132 and a second edge 134 each extending at least from the back surface 126 to the terminus 128 of the claw 106. It should be appreciated that the a first edge 132 is positioned on a first lateral side of the central axis 114, and the second edge 134 is positioned on a second lateral side of the central axis 114. The first edge 132 is aligned with a first edge 136 of the main body 104, and the second edge 134 is aligned with a second edge 138 of the main body 104. In some embodiments, the jaws 116, 118 are formed as a single monolithic component with the main body 104, and in other embodiments, the jaws 116, 118 are separate components from the main body 104 and coupled thereto.

Referring still to FIGS. 1 and 2, the absorbent material 11 includes a first edge 140 and a second edge 142 each extending between the front and back ends 122, 124 of the absorbent material 11. In the illustrative embodiment, the components are be sized and shaped such that the first edge 140 of the absorbent material 11 is aligned (i.e. flush) with the first edge 132 of the jaw 116 and the second edge 142 of the absorbent material 11 is aligned (i.e. flush) with the second edge 134 of the jaw 116 when the absorbent material is positioned in gap 120. In some embodiments, the components may be sized and shaped such that one or both edges 140, 142 of the absorbent material 11 extend beyond the first or second edge 132, 134 respectively of the jaw 116. It should be appreciated that the orientation, size, and shape of the absorbent material 11 relative to the jaws 116, 118 are not arbitrary and are important for providing the optimal drug delivery to the tissue of a patient's eye.

The top jaw 116 further includes a top surface 146 defining a top surface 148 of the claw 106 and a bottom surface 150 opposite the top surface 146. As is consistent with the "mirror image" description herein, the bottom jaw 118 includes a bottom surface 156 defining a bottom surface 154 of the claw 106 and a top surface 152 opposite the bottom surface 156. The absorbent material 11 further includes a top surface 160 and a bottom surface 162. The top surface 160 of the absorbent material 11 is urged against the bottom surface 150 of the top jaw 116 when the absorbent material 11 is positioned in the gap 120. The bottom surface 162 of the absorbent material 11 is urged against the top surface 152 of the bottom jaw 118 when the absorbent material 11 is positioned in the gap 120.

In some embodiments, the claw 106 is formed as a single monolithic component with the main body 104. In some embodiments, the claw 106 is a separate component from the main body 104 that may be coupled thereto. In some embodiments, the applicator assembly 10 includes the claw 106 and other claws. The claw 106 may be removed from the first side 102 of the main body 104, and another claw may be coupled to the first side 102 of the main body 104. In some embodiments, the claw 106 is the only claw included in the applicator assembly 10.

Figure 3:
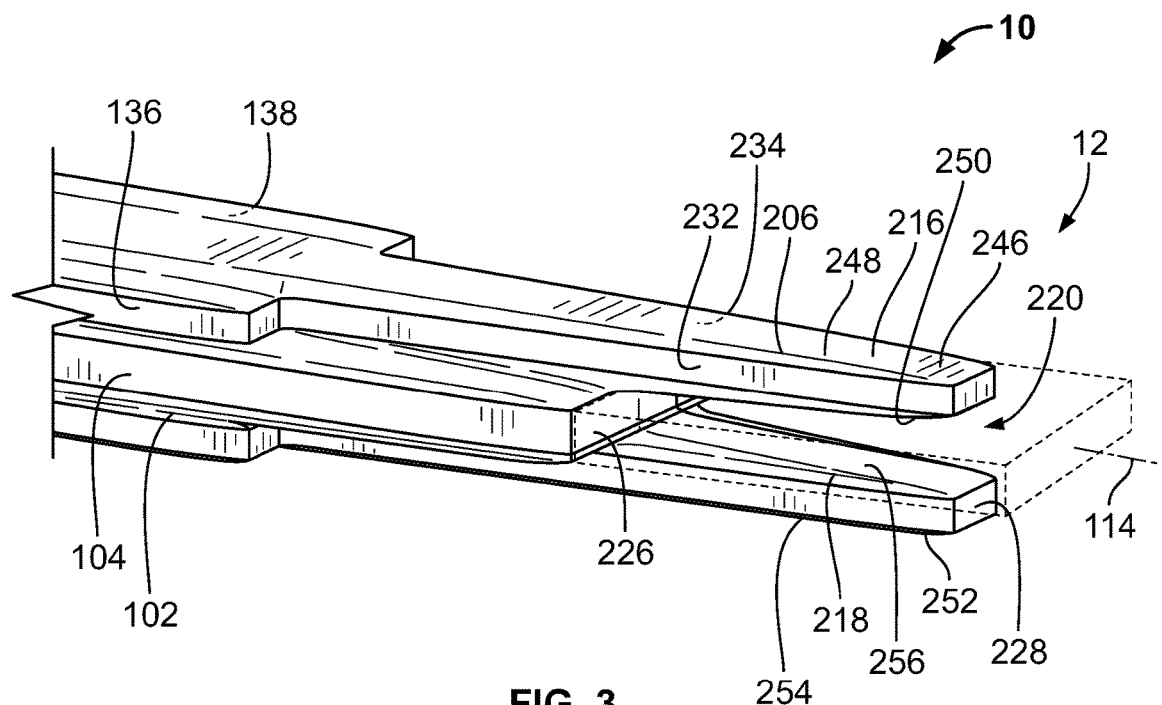
FIG. 3 is a perspective view of a portion of another pincher rod.

Referring now to FIG. 3, a claw 206 of the pincher rod 12 is shown. In some embodiments, the applicator assembly 10 includes the claw 106 and other claws, such as the claw 206. The claw 106 may be removed from the first side 102 of the main body 104. Another claw, such as the claw 206, may be coupled to the first side 102 of the main body 104. In some embodiments, the pincher rod 12 does not include multiple claws and only includes the claw 206. In some embodiments, the claw 206 is formed as a single monolithic component with the main body 104. In some embodiments, the claw 206 is a separate component from the main body 104 that may be coupled thereto.

As shown in FIG. 3, the claw 206 includes a top jaw 216 and a bottom jaw 218 each extending away from the main body 104 substantially parallel to the central axis 114. The top jaw 216 and the bottom jaw 218 are spaced apart vertically (as oriented in FIG. 3) to define a gap 220 therebetween. The central axis 114 extends through the gap 220. The absorbent material 11 is positionable in the gap 220 such that the central axis 114 extends through the absorbent material 11 when the absorbent material 11 is coupled to the pincher rod 12. In some embodiments, the jaws 216, 218 are flexible such that the gap 220 may be expanded to position the absorbent material 11 therein. In some embodiments, the absorbent material 11 is compressible. In any event, the absorbent material is secured with the gap 220 as a result of a compressive force applied by the jaws 216, 218 to the absorbent material 11.

The back end 124 of the absorbent material 11 may abut and/or be positioned adjacent to a back surface 226 of the claw 206 that is positioned between the top and bottom jaws 216, 218. Each jaw 216, 218 extends from the back surface 226 to a terminus 228 of the claw 206. In some embodiments, the front end 122 of the absorbent material 11 extends beyond the terminus 228 of the claw 206.

As suggested by FIG. 3, the top and bottom jaws 216, 218 are oriented such that they are mirror images of one another and are otherwise substantially identical; therefore, any description of the top jaw 216 applies equally to the bottom jaw 218. The jaw 216 includes a first edge 232 and a second edge 234 each extending at least from the back surface 226 to the terminus 228 of the claw 206. It should be appreciated that the a first edge 232 is positioned on a first lateral side of the central axis 114, and the second edge 234 is positioned on a second lateral side of the central axis 114. In some embodiments, the edges 232, 234 extend away from the terminus 228 beyond the back surface 226 of the claw 206. The first edge 232 is set in from the first edge 136 of the main body 104 (laterally nearer to the central axis 114), and the second edge 234 is set in from the second edge 138 of the main body 104 (laterally nearer to the central axis 114).

In the illustrative embodiment, the components may be sized and shaped such that the first edge 140 of the absorbent material 11 is positioned outward of (or further from the central axis 114 in the lateral direction relative to) the first edge 232 of the jaw 216 when the absorbent material is positioned in gap 220. The second edge 142 of the absorbent material 11 is positioned outward of (or further from the central axis 114 in the lateral direction relative to) the second edge 234 of the jaw 216 when the absorbent material is positioned in gap 120. In some embodiments, the components may be sized and shaped such that the first and second edges 140, 142 of the absorbent material 11 are aligned with the first and second edges 232, 234 respectively of the jaw 216. It should be appreciated that the orientation, size, and shape of the absorbent material 11 relative to the jaws 216, 218 are not arbitrary and are important for providing the optimal drug delivery to the tissue of a patient's eye.

The top jaw 216 further includes a top surface 246 defining a top surface 248 of the claw 206 and a bottom surface 250 opposite the top surface 246. As is consistent with the "mirror image" description herein, the bottom jaw 218 includes a bottom surface 252 defining a bottom surface 254 of the claw 206 and a top surface 256 opposite the bottom surface 252. The top surface 160 of the absorbent material 11 is urged against the bottom surface 250 of the top jaw 216 when the absorbent material 11 is positioned in the gap 220. The bottom surface 162 of the absorbent material 11 is urged against the top surface 256 of the bottom jaw 218 when the absorbent material 11 is positioned in the gap 220.

Figure 4:
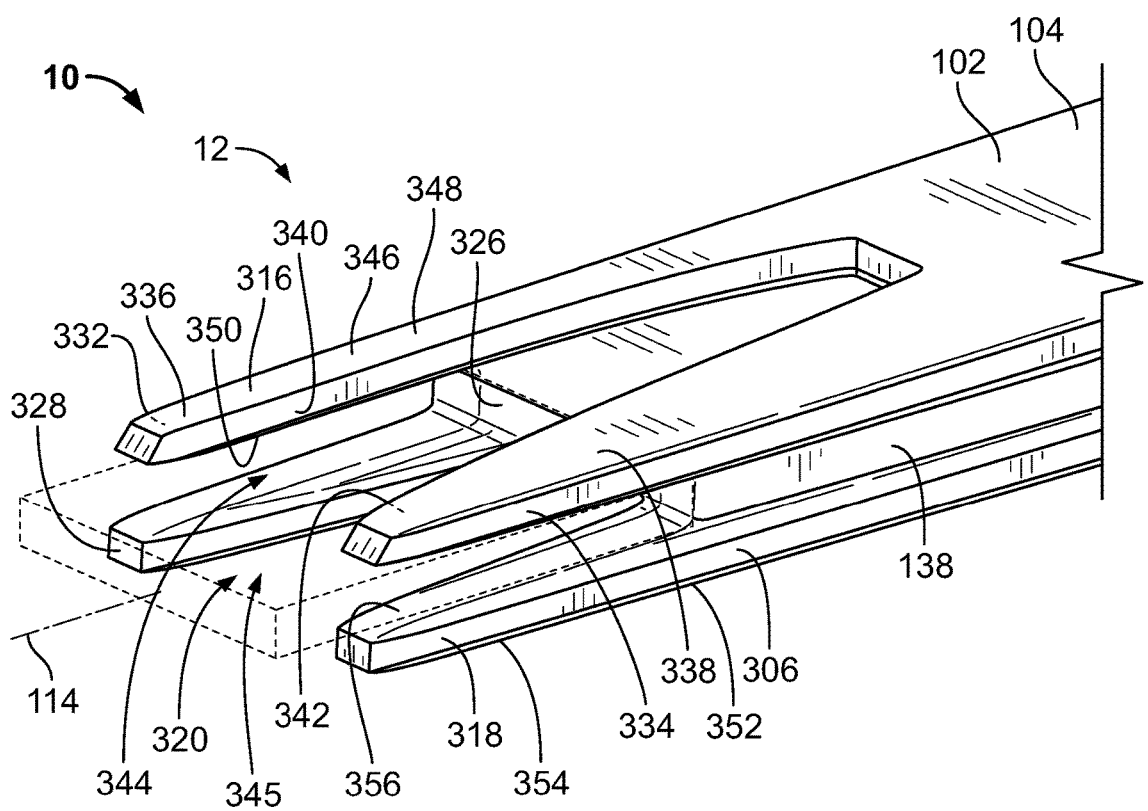
FIG. 4 is a perspective view of a portion of another pincher rod.

Referring now to FIG. 4, a claw 306 of the pincher rod 12 is shown. In some embodiments, the applicator assembly 10 includes the claws 106 and/or 206 and other claws, such as the claw 306. The claw 106 or 206 may be removed from the first side 102 of the main body 104. Another claw, such as the claw 306, may be coupled to the first side 102 of the main body 104. In some embodiments, the pincher rod 12 does not include multiple claws and only includes the claw 306. In some embodiments, the claw 306 is formed as a single monolithic component with the main body 104. In some embodiments, the claw 306 is a separate component from the main body 104 that may be coupled thereto.

As shown in FIG. 4, the claw 306 includes a top jaw 316 and a bottom jaw 318 each extending away from the main body 104 substantially parallel to the central axis 114. The top jaw 316 and the bottom jaw 318 are spaced apart vertically (as oriented in FIG. 4) to define a gap 320 therebetween. The central axis 114 extends through the gap 320. The absorbent material 11 is positionable in the gap 320 such that the central axis 114 extends through the absorbent material 11 when the absorbent material 11 is coupled to the pincher rod 12. In some embodiments, the jaws 316, 318 are flexible such that the gap 320 may be expanded to position the absorbent material 11 therein. In some embodiments, the absorbent material 11 is compressible. In any event, the absorbent material 11 is secured within the gap 320 as a result of a compressive force applied by the jaws 316, 318 to the absorbent material 11.

The back end 124 of the absorbent material 11 may abut and/or be positioned adjacent to a back surface 326 of the claw 306 that is positioned between the top and bottom jaws 316, 318. Each jaw 316, 318 extends at least from the back surface 326 to a terminus 328 of the claw 306. In some embodiments, the front end 122 of the absorbent material 11 extends beyond the terminus 328 of the claw 306.

As suggested by FIG. 4, the top and bottom jaws 316, 318 are oriented such that they are mirror images of one another and are otherwise substantially identical; therefore, any description of the top jaw 316 applies equally to the bottom jaw 318. The jaw 316 includes a first outer edge 332 and a second outer edge 334 each extending at least from the back surface 326 to the terminus 328 of the claw 306. It should be appreciated that the a first edge 332 is positioned on a first lateral side of the central axis 114, and the second edge 334 is positioned on a second lateral side of the central axis 114 In some embodiments, the edges 332, 334 extend away from the terminus 328 beyond the back surface 326 of the claw 306. The first outer edge 332 is aligned (i.e. flush) with the first edge 136 of the main body 104, and the second outer edge 334 is aligned (i.e. flush) with the second edge 138 of the main body 104.

In the illustrative embodiment, the components are sized and shaped such that the first edge 140 of the absorbent material 11 is aligned with the first edge 332 of the jaw 316 and the second edge 142 of the absorbent material 11 is aligned with the second edge 334 of the jaw 316 when the absorbent material is positioned in gap 120. It should be appreciated that the orientation, size, and shape of the absorbent material 11 relative to the jaws 316, 318 are not arbitrary and are important for providing the optimal drug delivery to the tissue of a patient's eye.

It should also be appreciated that the top jaw 316 includes a top surface 346 defining a portion of a top surface 348 of the claw 306 and a bottom surface 350 opposite the top surface 348. As is consistent with the "mirror image" description herein, the bottom jaw 318 includes a bottom surface 352 defining a bottom surface 354 of the claw 306 and a top surface 356 opposite the bottom surface 352. In some embodiments, the components are sized and shaped such that the top surface 160 of the absorbent material 11 is aligned (i.e. flush) with the top surface 348 of the claw 306, and the bottom surface 162 of the absorbent material 11 is aligned (i.e. flush) with the bottom surface 354 of the claw 306.

In some embodiments, the absorbent material 11 is cuboid-shaped such that only one of: (a) the top and bottom surfaces 160, 162, or (b) the edges 140, 142 of the absorbent material 11 are aligned (i.e. flush) with the respective surfaces 348, 354 or the edges 332, 334 of the claw 306. In other embodiments, the absorbent material 11 is plus-sign-shaped such that both of: (a) the top and bottom surfaces 160, 162, or (b) the edges 140, 142 of the absorbent material 11 are aligned (i.e. flush) with the respective surfaces 348, 354 or edges 132, 134 of the claw 306. What is meant by "cuboid-shaped" is that when the absorbent material is coupled to the pincher rod 12 and viewed in a plane perpendicular to the central axis 114, the absorbent material 11 is rectangular. What is meant by "plus-sign-shaped" is that when the absorbent material 11 is coupled to the pincher rod 12 and viewed in a plane perpendicular to the central axis 114, the absorbent material is shaped as a plus sign (+).

The top jaw 316 includes a first arm 336 and a second arm 338 spaced apart from the first arm 336. The first arm 336 includes the first outer edge 332 of the claw 306, and the second arm 338 includes the second outer edge 334 of the claw 306. The first arm 336 further includes a first inner edge 340, and the second arm 338 includes a second inner edge 342. The first and second inner edges 340, 342 define a gap 344 therebetween. A gap 345 is likewise formed between the inner surfaces of the arms of the bottom jaw 318. In embodiments where the top and bottom surfaces 160, 162 of the absorbent material are aligned (i.e. flush) with the respective surfaces 348, 354 of the claw 306, a portion of the absorbent material 11 is positioned in one or both gaps 344, 345.

Figure 5:
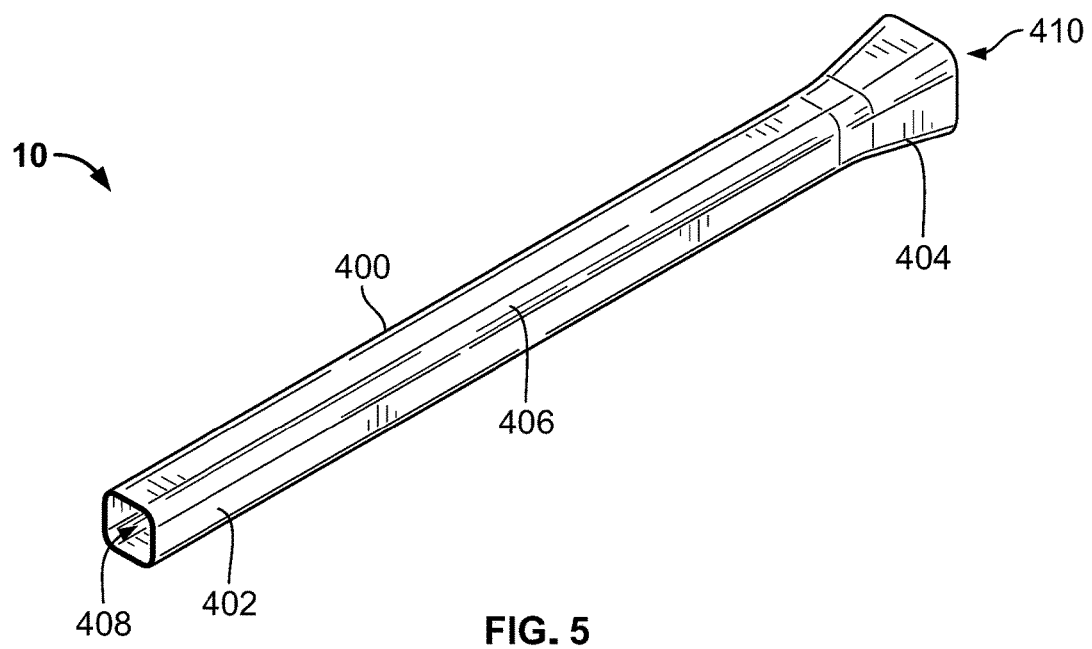
FIG. 5 is a perspective view of a hollowing casing, sometimes referred to as an outer cylindrical casing, of the applicator assembly.

FIG. 5 shows a casing 400 for the applicator assembly 10. The casing 400 is a hollow, elongated shaft having a first end 402, a second end 404, and a middle portion 406. The first end 402 defines a first opening 408 sometimes referred to as a window 15 or an aperture 15b of the window 15. In any event, the first opening 408 opens to a hollow center of the middle portion 406. The second end 404 defines a second opening 410 opening to the hollow center of the middle portion 406. In some embodiments, the second opening 410 has a perimeter larger than the perimeter of the middle portion 406 of the casing 400. As such, the second end 404 has a flared shape. In some embodiments, the second end 404 does not have a flared shape, and the opening 410 has a perimeter equal to the perimeter of the middle portion 406.

Figure 6:
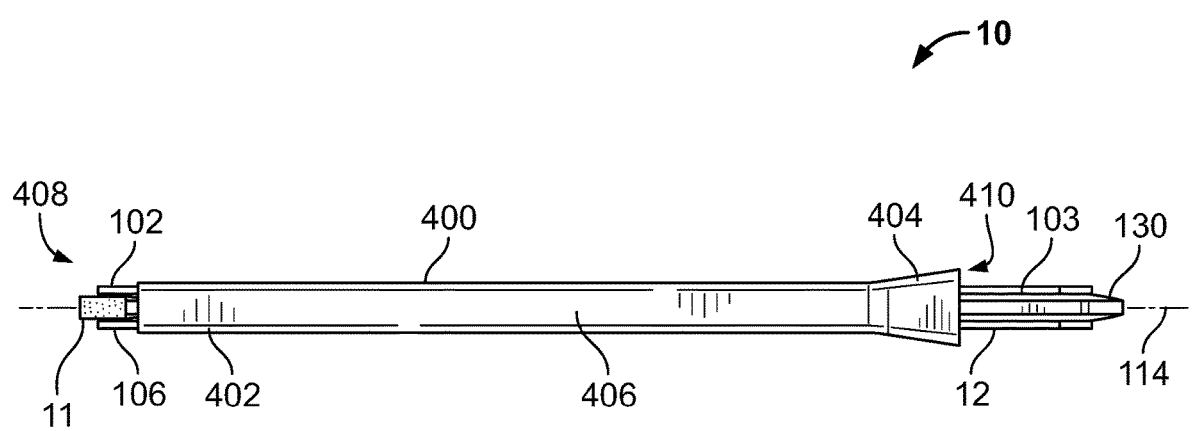
FIG. 6 is a side view of the absorbent material and the pincher rod of FIG. 2, showing the pincher rod positioned within the outer casing of FIG. 5.

FIG. 6 shows the absorbent material 11 coupled to the pincher rod 12 and the pincher rod 12 positioned within the hollow casing 400. In use, the first end 102 of the pincher rod 12 may be inserted into the second end 404 of the casing 400. The pincher rod 12 may be advanced through the hollow casing 400 until the first end 102 of the pincher rod 12 (and the absorbent material 11 coupled thereto) extend through the opening 408 and beyond the first end 402 of the casing 400. A user may grip the tab 130 or any component coupled thereto to move the pincher rod 12 forward and rearward relative to the casing 400 along the central axis 114. In this manor, drug or other agent on the absorbent material 11 may be applied to a tissue surface of a patient. After the drug or other agent has been applied, the pincher rod 12 may be pulled rearward back through the casing 400 to remove the absorbent material 11 from the tissue surface of the patient, and then to remove the absorbent material from the pincher rod 12.

While the claw 106 is illustratively shown coupled to the pincher rod 12 in FIG. 6, it should be appreciated that the claw 206 or claw 306 may be attached to the pincher rod 12 instead. In some embodiments, the applicator assembly 10 includes the casing 400 and other casings. The pincher rod 12 may be removed from the casing 400 and inserted into another casing. In some embodiments, the applicator assembly 10 does not include multiple casings and only includes the casing 400.

Figure 7:
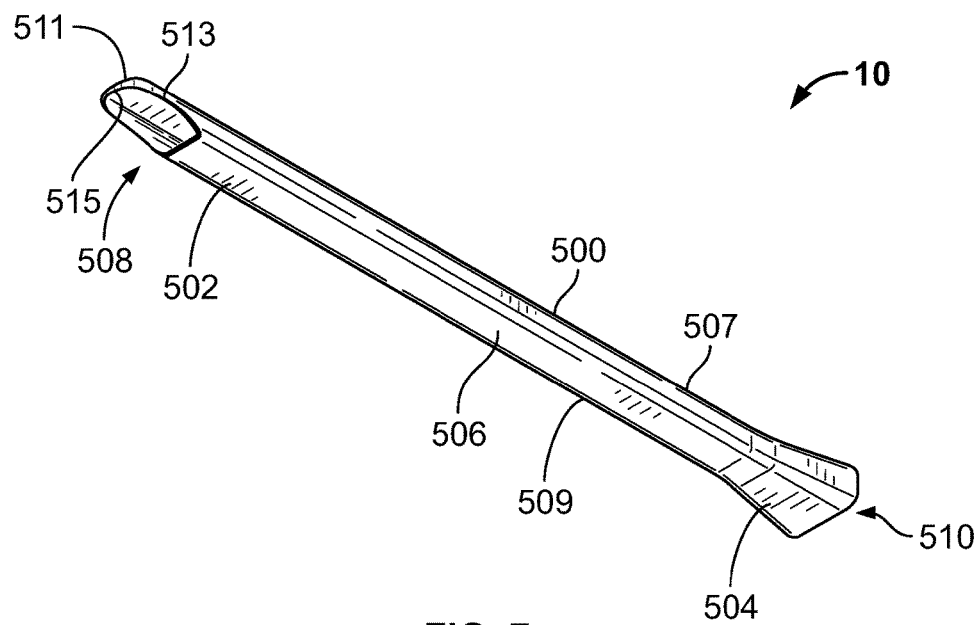
FIG. 7 is a perspective view of another hollow casing of the applicator assembly, showing that the hollow casing is formed to include a downward-facing opening to expose the absorbent material to tissue of a patient's eye.

FIG. 7 shows a casing 500 for the applicator assembly 10. The casing 500 is a hollow, elongated shaft having a first end 502, a second end 504, and a middle portion 506. The casing 500 further includes a top side 507 and a bottom side 509. The first end 502 includes a first opening 508 defined therein and sometimes referred to as a window 15 or an aperture 15b of the window 15. In any event, the first opening 508 opens to a hollow center of the middle portion 506. The first opening 508 is a formed by a void in the bottom side 509 of casing 500. Thus, the opening 508 opens downward based on the orientation of the casing 500 shown in FIGS. 7 and 8a-b. The top side 507 of the casing 500 extends to a terminus 511. The terminus 511 is defined in end wall 513 extending downward from the top side 507. The end wall 513 is U-shaped and includes an inner surface 515 facing toward the hollow center of the middle portion 506. The end wall 513 defines a portion or boundary of the opening 508.

The second end 504 defines a second opening 510 opening to the hollow center of the middle portion 506. In some embodiments, the second opening 510 has a perimeter larger than the perimeter of the middle portion 506 of the casing 500. As such, the second end 504 has a flared shape. In some embodiments, the second end 504 does not have a flared shape, and the opening 510 has a perimeter equal to the perimeter of the middle portion 506.

Figure 8A:
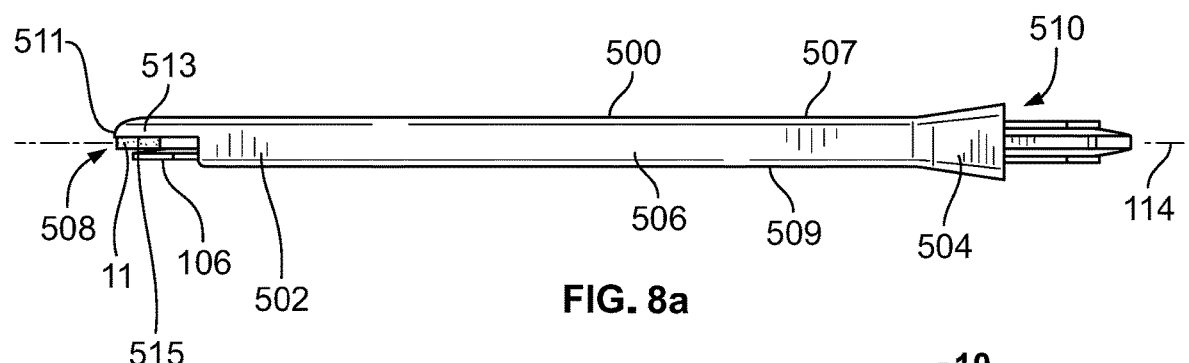
FIG. 8*a* is a side view of the absorbent material and the pincher rod of FIG. 2 and the hollow casing of FIG. 7.

FIG. 8a shows the absorbent material 11 coupled to the pincher rod 12 and the pincher rod 12 positioned within the hollow casing 500. In use, the first end 102 of the pincher rod 12 may be inserted into the second end 504 of the casing 500. The flare second end 504 may first contact the pincher rod 12 or the absorbent material 11 to guide the pincher rod 12 into the hollow center of the casing 500. The pincher rod 12 may be advanced through the hollow casing 500 until the first end 102 of the pincher rod 12 (and the absorbent material 11 coupled thereto) extend beyond the bottom side 509 of the casing 500. At this point the absorbent material is positioned adjacent the void defined in the bottom side 509 of the casing 500. A user may grip the tab 130 or any component coupled thereto to move the pincher rod 12 forward and rearward relative to the casing 500 along the central axis 114. The pincher rod 12 may be advanced forward along the central axis 114 until the absorbent material 11 contacts the inner surface 515 of the end wall 513.

Figure 8B:
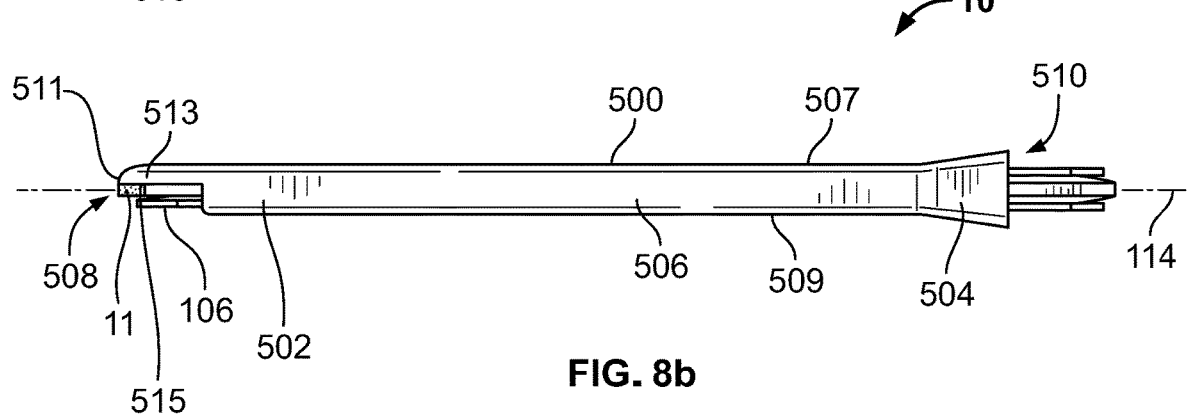
FIG. 8*b* is a side view of the components of FIG. 8*a* showing the absorbent material compressed by an end wall defining the downward-facing opening.

As shown in FIG. 8b, the pincher rod 12 may be advance further forward to urge the absorbent material 11 against the end wall 513 to compress the absorbent material 11. The compression of the absorbent material 11 between the end wall 513 and the claw 106 causes drug or agent to be excreted from the absorbent material 11. The excreted drug or agent may pass through the downward facing opening 508. In this manor, drug or other agent on the absorbent material 11 may be applied to a tissue surface of a patient. After the drug or other agent has been applied, the pincher rod 12 may be pulled rearward back through the casing 500.

In some embodiments, the absorbent material 11 may directly contact the tissue of a patient when the absorbent material 11 is positioned adjacent the void defined in the bottom side 509 of the casing 500.

While the claw 106 is illustratively shown coupled to the pincher rod 12 in FIG. 8a-b, it should be appreciated that the claw 206 or claw 306 may be attached to the pincher rod 12 instead. In some embodiments, the applicator assembly 10 includes the casing 500 and other casings, for example, the casing 400. The pincher rod 12 may be removed from the casing 500 and inserted into another casing such as the casing 400. In some embodiments, the applicator assembly 10 does not include multiple casings and only includes the casing 500.

FIGS. 9a and 9b show a casing 600 for the applicator assembly 10, with the pincher rod 12 positioned therein. The casing 600 is similar to the casing 500, except that the window 15 of the casing 600 is a retractable window. Some components of the casing 600 are substantially identical to components of the casing 500, and therefore, in some instances, reference numbers are repeated to indicate the commonality. The casing 600 includes a retractable cover 650 positioned adjacent the bottom side 509 of the casing 600. The retractable cover 650 is movable from a closed position 660 (see FIG. 9a) to an open position 662 (see FIG. 9b).

FIG. 9a shows the retractable cover 650 in the closed position 660. In the closed position 660, the retractable cover 650 extends to the terminus 511 of the casing 600 and covers the opening 508. As such, the absorbent material 11 is separated from a patient's tissue via the retractable cover 650 when the retractable cover is in the closed position 660. The casing 600 further includes an actuator 652 having a tab 654. The actuator 652 may be moved when a user adjusts the tab 654 from a first position 670 (see FIG. 9a) to a second position 672 (see FIG. 9b). The actuator 652 is coupled at a first end to the tab 654 and at a second end to the retractable cover 650; therefore, when the tab 654 is moved from the first position 670 to the second position 672, the actuator 652 moves the retractable cover 650 from the closed position 660 to the open position 662.

FIG. 9b shows the retractable cover 650 in the open position 662 and the tab 654 in the second position 672. In use, a user may pull the tab 654 rearwardly or otherwise adjust the tab 654 to move the tab 654 from the first position 670 to the second position 672. When the tab 654 is in the second position 672, the retractable cover 650 is in the open position 662, and drug or agent may be delivered to a tissue surface of a patient by any means described herein. After the drug or agent has been delivered, a user may move the tab 654 from the second position 672 to the first position 670 to cause movement of the retractable cover 650 from the open position 662 to the closed position 660. The pincher rod 12 may be removed from the casing 600. The claw 106 may be decoupled from the casing 600 and different claw 206 or 306 may be coupled to the pincher rod 12. This process may be repeated to provide various drugs or agents to various portions of a patient's tissue with the applicator assembly 10.

In some embodiments, the applicator assembly 10 includes the casing 600 and other casings, for example, the casings 400 and 500. The pincher rod 12 may be removed from the casing 600 and inserted into another casing such as the casing 400 or 500. In some embodiments, the applicator assembly 10 does not include multiple casings and only includes the casing 600.

Figure 10:
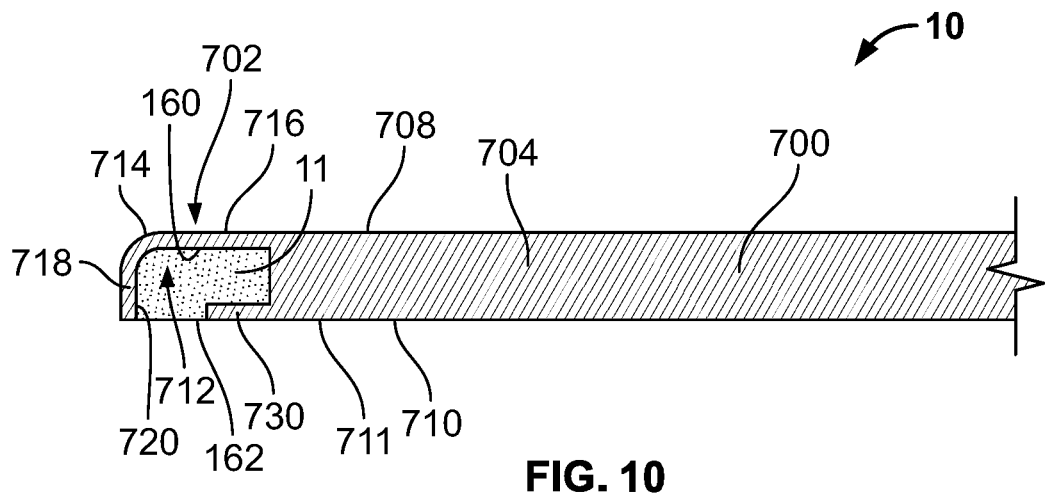
FIG. 10 is a cross section view of a shielding rod and absorbent material positioned at a distal end of the shielding rod.

In another embodiment, the applicator assembly 10 includes the casing 400 (see FIG. 5) and a shielding rod 700 as shown in FIG. 10. As described above and shown in FIGS. 12-13, the casing 400 is a hollow, elongated shaft having a first end 402, a second end 404, and a middle portion 406. The first end 402 defines a first opening 408. The first opening 408 opens to a hollow center of the middle portion 406. The second end 404 defines a second opening 410 opening to the hollow center of the middle portion 406. In some embodiments, the second opening 410 has a perimeter larger than the perimeter of the middle portion 406 of the casing 400. As such, the second end 404 has a flared shape. In some embodiments, the second end 404 does not have a flared shape, and the opening 410 has a perimeter equal to the perimeter of the middle portion 406.

As illustratively shown in FIG. 10, the absorbent material 11 may be positioned at a distal end 702 of the shielding rod 700. In some embodiments, the absorbent material 11 is permanent fixed to the shielding rod 700, and in some embodiments, the absorbent material 11 is removable from the shielding rod 700 and may be replaced with another absorbent material 11. In any event, the shielding rod 700 includes a main body 704, the distal end 702, and a proximal end 706 opposite the distal end 702. The shielding rod 700 includes a top side 708 and a bottom side 710 opposite the top side 708.

A cavity 712 is defined at the distal end 702 of the shielding rod 700. The cavity 712 is sometimes referred to as a window 15 or an aperture 15b of the window 15. In any event, the cavity 712 is sized and shaped to receive the absorbent material 11. The cavity 712 opens downward based on the orientation of the shielding rod 700 shown in FIGS. 10-13. Thus, when the absorbent material 11 is positioned in the cavity 712, the absorbent material 11 is eclipsed by the shielding rod 700 when the shielding rod 700 is viewed from a top down perspective, but the absorbent material 11 is visible when the shielding rod 700 is viewed from a bottom up perspective. What is meant by "eclipsed" is hidden from view.

The shielding rod 700 further includes a shield 714 defined at the distal end 702 thereof. The shield 714 cooperates with the main body 704 to form the cavity 712. The shield 714 includes a top portion 716 coupled to the main body 704 and extending distally away from the main body 704. The top portion 716 of the shield 714 is defined at the top side 708 of the shielding rod 700. In embodiments in which the shield 714 is removably coupled to the shielding rod 700, it may be said that the top portion 716 of the shield 714 is aligned with the top side 708 of the shielding rod 700 when the shield 714 is coupled to the shielding rod 700. In any event, the top portion 716 of the shield 714 defines a portion of the cavity 712.

In some embodiments, the shield 714 includes an end wall 718 extending downward from the top portion 716 of the shield 714 and cooperating to define the cavity 712. The end wall 718 is U-shaped and includes an end portion 719 having an inner surface 720 facing toward the main body 704 of the shielding rod 700. The U-shaped end wall 718 also includes first and second legs 722, 724 positioned on first and second sides 726, 728 of the shielding rod 700 and extending between the inner surface 714 of the end wall 718 and the main body 700.

The U-shaped end wall 718 eclipses the absorbent material 11 when the shielding rod 700 is viewed in a plan view from a position distal to the shielding rod 700 and when the shielding rod 700 is viewed in plan view looking at either side 726, 728 of the shielding rod 700. The U-shaped end wall 718 and the top portion 716 therefore prevent the absorbent material 11 from contacting tissue except with the bottom surface 162 of the absorbent material 11 when the applicator assembly 10 is in use.

As illustratively shown in FIGS. 10-13, when the absorbent material 11 is coupled to the shielding rod 700, the top portion 716 of the shield 714 is positioned above the absorbent material 11. The top portion 716 of the shield 714 is directly adjacent the absorbent material 11. The top portion 716 of the shield 714 is positioned nearer to the top side 708 of the shielding rod 700 than the absorbent material 11. The absorbent material 11 is positioned nearer to the bottom side 710 of the shielding rod 700 than the top portion 716 of the shield 714.

In some embodiments, the absorbent material extends from the top portion 716 of the shield 714 to the bottom side 710 of the shielding rod 700 and is flush with a bottom surface 711 of the bottom side 710. In other embodiments, the absorbent material 11 is not flush with the bottom surface 711.

In any event, when the absorbent material 11 is coupled to the shielding rod 700, the absorbent material 11 is eclipsed by the top portion 716 of the shield 714 when the shielding rod 700 is viewed from a top down perspective. The top portion 716 of the shield 714 prevents the top surface 160 of the absorbent material 11 from contacting tissue when the apparatus 10 is in use.

In some embodiments, as illustrative shown in FIG. 10, the shield 714 may further include a bottom portion 730 coupled to the main body 704 and extending distally away from the main body 704. The bottom portion 730 of the shield 714 is defined at the bottom side 710 of the shielding rod 700. When the absorbent material 11 is coupled to the shielding rod 700, the absorbent material 11 is at least partially eclipsed by the bottom portion 730 of the shield 714 when the shielding rod 700 is viewed from a bottom up perspective.

Figure 13:
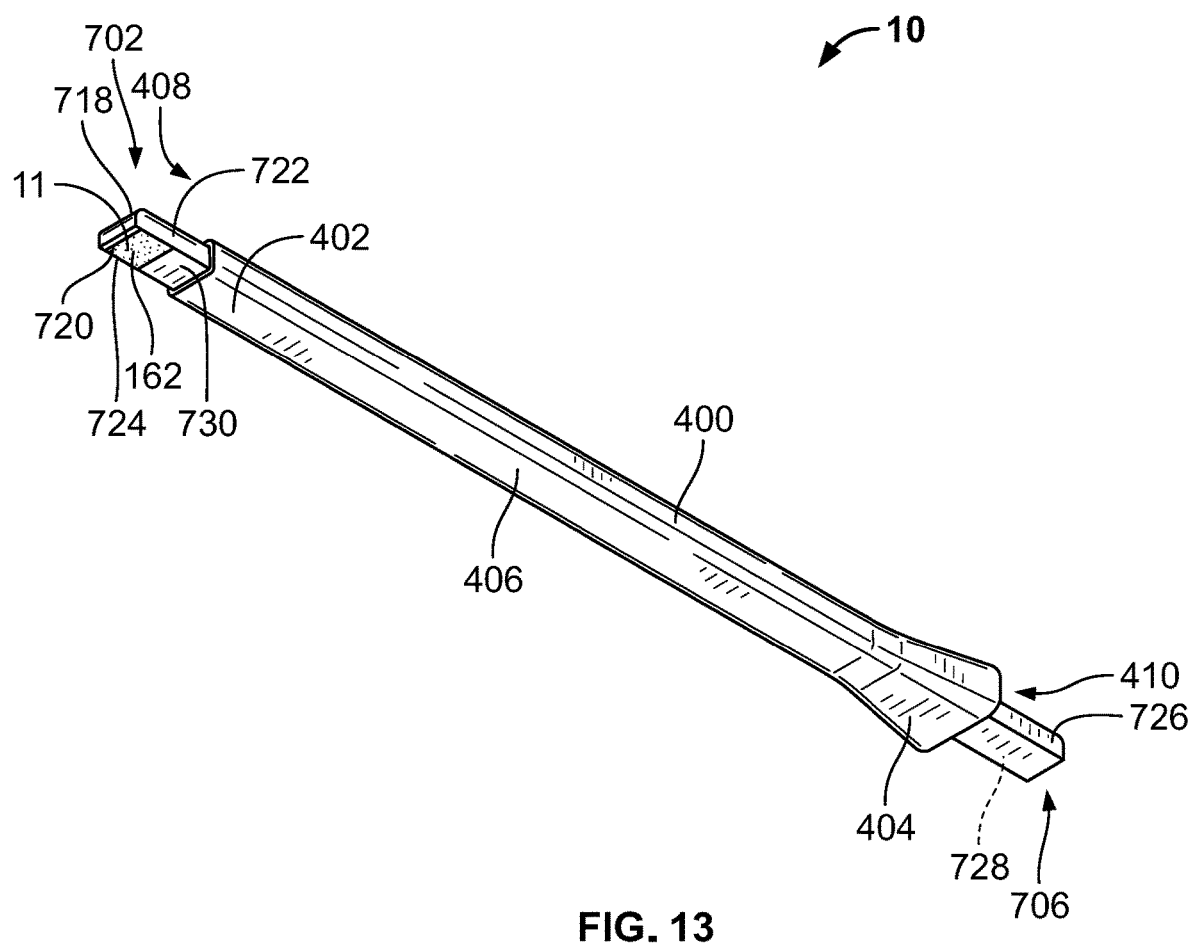
FIG. 13 is a perspective view of the components of FIG. 12.

In some embodiments, as shown in FIG. 13, the bottom portion 730 of the shield 714 is coupled to the legs 722, 724 of the U-shaped end wall 718. In this case, the bottom portion 730 of the shield 714 is spaced apart from the inner surface 720 of the end wall 718.

In some embodiments, the bottom portion 730 of the shield 714 is coupled to the legs 722, 724 of the U-shaped end wall 718 and coupled to the inner surface 720 of the end wall 718. In this case, the bottom portion 730 of the shield 714 is spaced apart from the main body 704.

In any event, the bottom portion 730 of the shield 714 cooperates with the top portion 716 of the shield 714 and the U-shaped end wall 718 to form the cavity 712. The shield 714 may be formed as a single monolithic component with the main body 704, or the shield 714 and the main body 704 may be formed as separate components and later assembled.

In some embodiments, the applicator assembly 10 may include multiple shields 714, and each shield 714 may have any of the configurations described above. In use, a first shield 714a may be coupled to the shielding rod 700. The first shield 714a may be removed from the shielding rod 700, and a second shield 714b may be coupled to the shielding rod 700, as will be described in greater detail below.

In some embodiments, the absorbent material 11 may be fixedly positioned in the cavity 712. In some embodiments, the absorbent material 11 may be removably coupled to the cavity 712. In use, a first absorbent material 11a is positioned in the cavity 712. The first absorbent material 11a may be removed from the cavity 712, and a second absorbent material 11b may be inserted in the cavity 712, as will be described in greater detail below.

The bottom portion 730 of the shield 714 determines the surface area of the absorbent material 11 that may be exposed to a patient's tissue. For example, in FIG. 10 lesser surface area of the absorbent material 11 is exposed than in FIG. 11. When less surface area of the absorbent material 11 is exposed, comparatively less drug is provided to the tissue, all other variables being equal. A maximum surface of area of the absorbent material 11 is exposed in embodiments including a shield 714 having no bottom portion 730 at all.

In use, a surface area of the absorbent material 11 required to be exposed may be predetermined based on several variables including, for example, a coefficient of absorption of the absorbent material 11, viscosity of the substance to be applied to a target region of a patient's tissue, surface area of the absorbent material 11 to be exposed to the patient's tissue, time of exposure, and concentration of the substance to be applied. It should be appreciated that the surface area to be exposed is synonymous with a portion of the bottom surface 162 of the absorbent material 11. In some embodiments, a diffusion rate may be calculated based on variables including, for example, the coefficient of absorption, the viscosity, and compression of the absorbent material 11.

Figure 11:
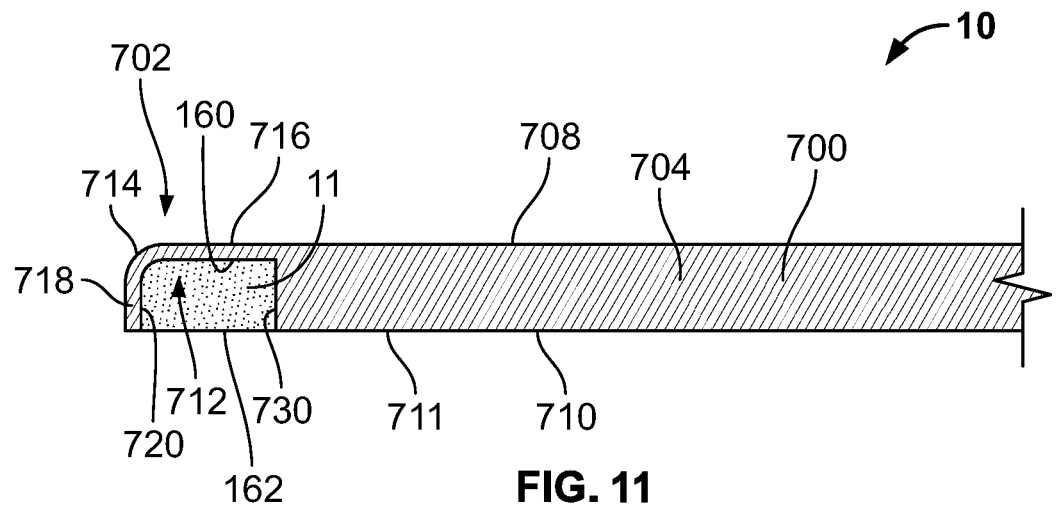
FIG. 11 is a cross section view of a shielding rod having a shield with a retractable and extendable bottom portion.

In some embodiments, the bottom portion 730 of the shield 714 is retractable and extendable to adjust the surface area of the absorbent material 11 exposable to the patient's tissue. FIG. 11 shows the bottom portion 730 of the shield 714 in a fully retracted position to expose a maximum surface area of the absorbent material 11. The bottom portion 730 of the shield 714 may also be movable to a fully extended position, in which no surface area of the absorbent material 11 is exposed.

Various structures may be used to retract and extend the bottom portion 730 of the shield 714, including for example, the components 652, 654 described with respect to FIGS. 9a and 9b. Such components may positioned at the bottom side 710 of the shielding rod 700.

Figure 12:
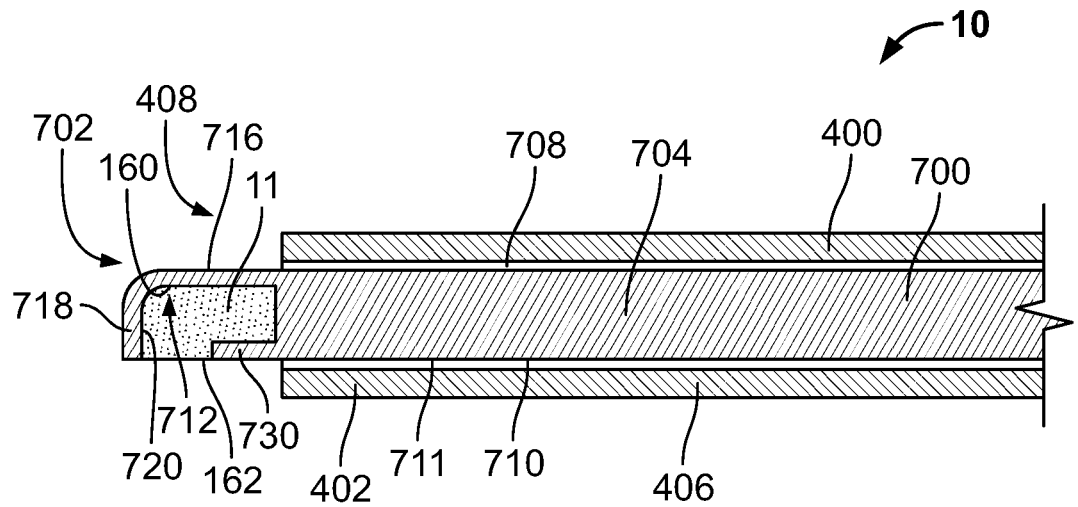
FIG. 12 is a cross section cut-off view of the shielding rod of FIG. 10 positioned inside the casing of FIG. 5.

FIGS. 12 and 13 illustrate the shielding rod 700 positioned in the casing 400. The shielding rod 700 is longer than the casing 400. Thus, when the shielding rod 700 positioned in the casing 400, the distal end 702 of the shielding rod 700 extends beyond the first side 402 of the casing 400, and the proximal end 706 of the shielding rod 700 extends beyond the second end 404 of the casing 400 (see FIG. 13).

In use, the distal end 702 of the shielding rod 700 may be inserted into the second opening 410 of the casing 400. A user may guide the distal end 702 of the shielding rod 700 into the second opening 410 of the casing 400 by contacting the flared second end 404 of the casing 400 with the a portion of the shielding rod 700. The shielding rod 700 may be advanced through the hollow center portion 406 of the casing 400 until the distal end 702 of the shielding rod 700 protrudes through the opening 408 and beyond the first end 402 of the casing 400. At this point, an exposed surface area of the absorbent material 11 is positioned outside the casing 400 such that it may be placed in contact with a patient's tissue.

In some embodiments, the shielding rod 700 may be a first shielding rod 700a coupled to a first absorbent material 11a. The first shielding rod 700a and first absorbent material 11a may be retracted and removed from the casing 400. A new shielding rod 700b having a new absorbent material 11b coupled thereto may be inserted into the casing 400.

In some embodiments, the shielding rod 700 is coupled to a first absorbent material 11a. The absorbent material 11a may be positioned adjacent to (and more specifically below) the top portion 716 of the shield 714. The shielding rod 700 and the first absorbent material 11a may be retracted and removed from the casing 400. The first absorbent material 11a may be decoupled from the shielding rod 700. A new absorbent material 11b may be coupled to the shielding rod 700 adjacent the shield 714. The shielding rod 700 and the new absorbent material 11b coupled thereto may be inserted into the casing 400.

In some embodiments, the shielding rod 700 may be coupled to a first shield 714a. A first absorbent material 11a is coupled to the first shield 714a. The shielding rod 700 and the first absorbent material 11a may be retracted and removed from casing 400. The first shield 714a and the first absorbent material 11a coupled thereto may be decoupled from the shielding rod 700. A second shield 714b having a new absorbent material 11b coupled thereto may be coupled to the shielding rod 700. The shielding rod 700 and the new absorbent material 11b coupled thereto may be inserted into the casing 400.

While the shielding rod 700 has been described as including a cavity 712 opening downward based on the orientation of the shielding rod 700 described herein, it should be appreciated that, in some embodiments, the cavity 712 may open to the first or second side 726, 728 of the shielding rod 700. As such, the shield 714 may also be reoriented to accommodate the cavity 712 opening to the first or second side 726, 728 of the shielding rod 700. Additionally, in some embodiments, the shielding rod 700 may be reoriented relative to the casing 400 such that the cavity 712 opens upward rather than downward.

Figure 14:
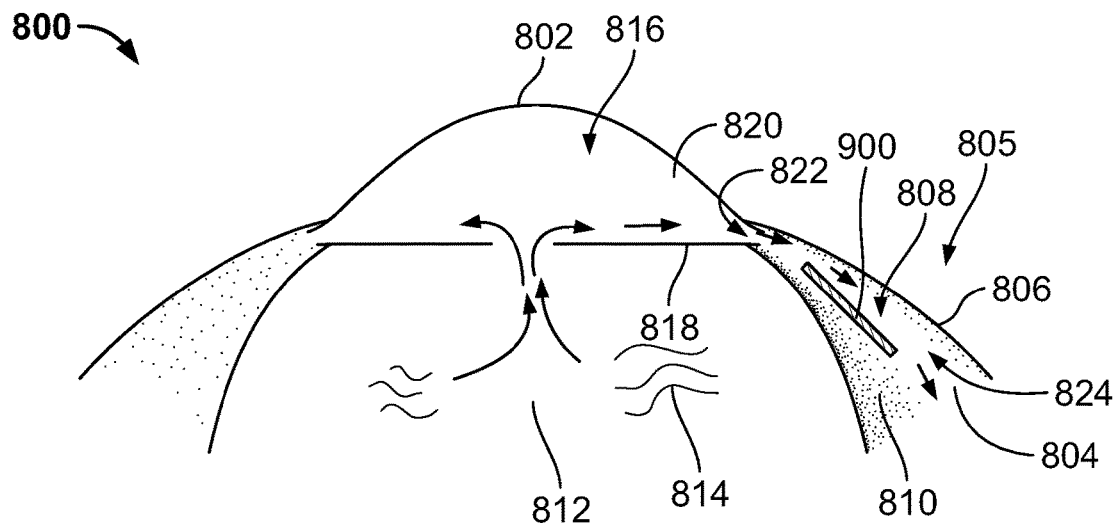
FIG. 14 is a top down view of an eye showing a target region for applying a drug.
Figure 15:
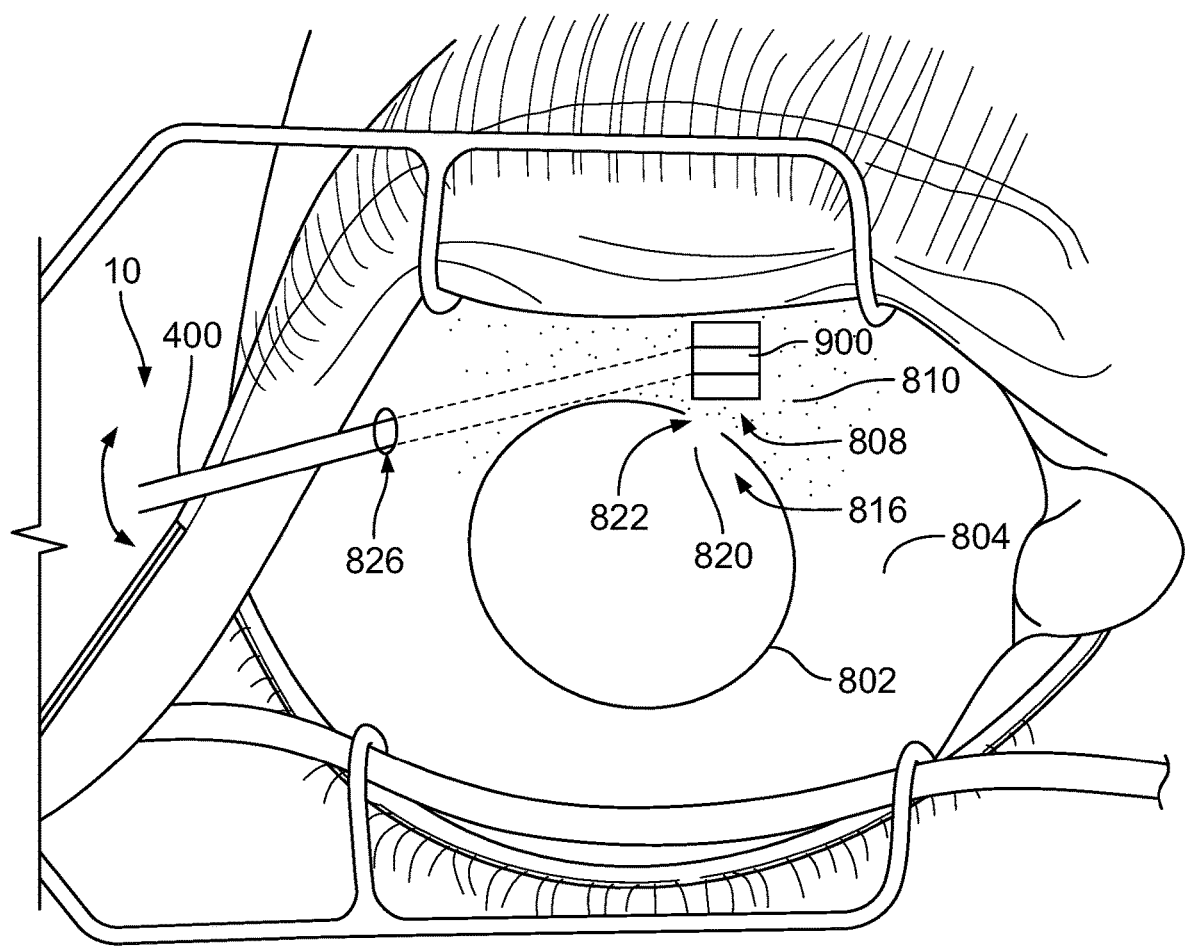
FIG. 15 is a front view of an eye showing a target region for a drug and the casing extending toward the target region.

Referring now to FIGS. 14 and 15, anatomy of the eye 800 is described to orient the applicator assembly 10 relative to the eye 800 when the applicator assembly 10 is in use. FIG. 14 shows a cross section view of the eye 800 from a top down perspective. The eye 800 include a cornea 802 and a sclera 804. A conjunctiva 806 is positioned adjacent the sclera 804. A bleb 805 may be formed in a subconjunctival space 808 defined between the conjunctiva 806 and the sclera 804. Fibroblasts 810 may be located in the subconjunctival space 808. The eye 800 may further include a vitreous body 812 including aqueous 814. An anterior chamber 816 may be formed inward of the cornea 802, and an iris 818 may formed generally between the anterior chamber 816 and the vitreous body 812. The eye 800 further includes a trabecular network 820 and a canal of Schlemm 822, which cooperate to define a passageway from the anterior chamber 816 to the subconjunctival space 808. The fibroblast 810 of the subconjunctival space 808 may proliferate or otherwise form a blockage preventing aqueous 814 from flowing out of the eye 800. This contributes to an increased pressure in the eye 800 (i.e. glaucoma).

In use, a surgeon may use the applicator assembly 10 to apply drug to a target region 900 defined in the subconjunctival space 808 to prevent the proliferation of fibroblasts 810, which ultimately reduces the likelihood of blockages forming in the subconjunctival space 808. Without blockages, aqueous 814 may flow out of the eye 800 to reduce pressure therein, thereby treating glaucoma.

In use, the surgeon may form a void 824 in the subconjunctival space 808 by displacing fibroblasts 810. Additionally, the surgeon may mark the target area 900, which may be along a boundary of the void 824, as suggested in FIG. 14. In some embodiments, the surgeon may mark, for example, three adjacent areas to which drug is to be applied (see FIG. 15). The areas may be for example, about 2×5 mm. In some embodiments, the markings may range from. Additionally, as shown in FIG. 15, the surgeon may create an incision 826 in the eye 800. The casing 400 may be inserted through the incision 826 and advanced toward the area of the eye 800 where the drug is to be applied.

After the target region 900 is marked, the surgeon may insert the shielding rod 700 (or another rod described herein) into the second opening 410 of the casing 400 and advance the shielding rod 700 distally toward the target region 900. It should be appreciated that at this point absorbent material 11 is coupled to the shielding rod 700. The shielding rod 700 is advanced distally until the distal end 702 of the shielding rod 700 protrudes from the opening 408 of the casing 400 and the bottom surface 162 of the absorbent material 11 contacts the target region 900. The absorbent material 11 is applied to a first of three 2×5 mm areas of the target region 900. No portion of the absorbent material 11 contacts portions of the eye 800 beyond the target region 900. For example, the shield 714 contacts non-targeted regions of the eye 800 to prevent the absorbent material 11 from contacting the non-targeted regions.

Non-targeted regions are regions of the eye 800 to which the drug or substance is not to be applied. For example, mitomycin C, or other substances are blocked from contacting non-targeted regions of the eye 800 because the shield 714 is positioned between the absorbent material 11 and the non-targeted region of the eye 800.

The surgeon may remove the shielding rod 700 from the casing 400. The casing 400 may be pivoted at the incision, according to the double-headed arrow shown in FIG. 15. A new absorbent material may be inserted into the casing 400. This may be accomplished by any of the sub-methods described above. For example: (i) a new shielding rod 700b having a new absorbent material 11b coupled thereto may be inserted into the casing 400; (ii) a new shield 714b having a new absorbent material 11b coupled thereto may be coupled to the previously inserted shielding rod 700a, and the previously-inserted shielding rod 700a may be inserted in the repositioned casing 400; or (iii) a new absorbent material 11b may be coupled to the previously-inserted shielding rod 700a with the previously-inserted shield 714a, and the previously-inserted shielding rod 700a may be inserted in the repositioned casing 400.

In any event, this process may be repeated for each separately-defined area of the target region 900. As such, a drug or substance, such as Myosin C, may be applied precisely and accurately to each separately-defined area of the target region 900.

By using a single casing 400 and multiple rods, shields, and/or absorbent materials, the incision 826 may remain its original size, which, for example, may be 3 mm in length. If a single casing 400 were not used, then the ingress and egress of each rod, shield, and/or absorbent material through the incision 826 multiple times would cause the incision 826 to expand to a much larger size, causing discomfort and eye damage to the patient. It should be appreciated that the casing 400 may have a dimension lesser than the, exemplary, 3 mm incision. For example It should be appreciated that any rod disclosed herein may be used in the surgical methods described with reference to the anatomy of the eye associated with FIGS. 14 and 15. Further, the applicator assembly 10 may include any of the rods, casings, and absorbent materials described herein.

The applicator assembly 10 may also include a spear rod and/or a glue rod. The spear rod may be a rod of any configuration described herein. In any event, the spear rod includes a tip positioned at the distal end of the rod, which is inserted into the absorbent material when the absorbent material is coupled to the rod. The tip may be a straight tip or a corkscrew tip. The glue rod may be a rod of any configuration described herein. In any event, the glue rod includes an adhesive substance coupling the absorbent material to the distal end of the rod.

Obviously, many variations and modifications of the present invention are possible in light of the above teachings, and it is to be construed that such variations and modifications are effectively to be included within the claimed method and apparatus. It is to be understood that within the scope of the appended claims, the present invention may be practiced otherwise than as specifically described herein.

The invention claimed is:

1. An applicator assembly comprising:
a hollow casing including a first end having a first opening defined therein and a second end having a second opening defined therein;
a shielding rod positioned within the hollow casing, configured to slide relative to the hollow casing, and including:
a top side and a bottom side opposite the top side;
a distal end, a proximal end opposite the distal end, and a main body positioned between the distal end and the proximal end;
a shield removably coupled to the main body at the distal end of the shielding rod, the shield including a top portion; and
an absorbent material including a top surface and a bottom surface;
wherein the absorbent material is coupled to the shield and positioned below the top portion of the shield with the top surface facing the top portion of the shield.

2. The applicator assembly of claim 1, wherein the top portion of the shield is aligned with the top side of the shielding rod when the shield is coupled to the shielding rod.

3. The applicator assembly of claim 1, wherein the shielding rod is formed to include a cavity defined in part by the top portion of the shield; and
wherein the absorbent material is positioned in the cavity.

4. The applicator assembly of claim 3, wherein the shield includes an end wall extending downward from the top portion of the shield and cooperating to define the cavity;
wherein the end wall is a U-shaped end wall including a pair of legs and an inner surface positioned between the pair of legs; and
wherein the pair of legs are positioned between the inner surface and the main body when the shield is coupled to the shielding rod.

5. The applicator assembly of claim 4, wherein the shield includes a bottom portion aligned with the bottom side of the shielding rod when the shield is coupled to the shielding rod; and
wherein the bottom surface of the absorbent material faces the bottom portion of the shield when the absorbent material is positioned in the cavity;
wherein, the bottom portion of the shield is coupled to the inner surface of the end wall;
wherein the bottom portion of the shield the extends proximally away from the inner surface toward the main body when the shield is coupled to the shielding rod; and
wherein the bottom portion of the shield is spaced apart from the shielding rod when the shield is coupled to the shielding rod.

6. The applicator assembly of claim 1, wherein the shield is a first shield; and
wherein the applicator assembly further comprises a second shield configured to be coupled to the shielding rod subsequent to the first shield being removed from the shielding rod.

7. A method of operating an applicator assembly comprising:
inserting a shielding rod having a first absorbent material coupled thereto into a hollow casing;
advancing the shielding rod through the hollow casing toward an opening of the hollow casing;
applying a substance carried by the first absorbent material to a first portion of patient's tissue;
retracting the shielding rod through the hollow casing away from the opening.

8. The method of claim 7, wherein the first portion of patient's tissue is a target region to which the drug is to be applied; and
wherein applying a substance carried by the first absorbent material to a first portion of patient's tissue includes:
contacting the target region with the first absorbent material, and
contacting a non-targeted region, to which the substance is not to be applied, with a shield of the shielding rod positioned adjacent the first absorbent material.

9. The method of claim 7, further comprising:
repositioning the hollow casing;
inserting the shielding rod into the hollow casing with a second absorbent material attached to the shielding rod;
advancing the shielding rod through the hollow casing toward the opening of the hollow casing;
applying a substance carried by the second absorbent material to a second portion of the patient's tissue; and
retracting the shielding rod through the hollow casing away from the opening.

10. The method of claim 9, further comprising:
repositioning the hollow casing;
inserting the shielding rod into the hollow casing with a third absorbent material attached to the shielding rod;
advancing the shielding rod through the hollow casing toward the opening of the hollow casing;
applying a substance carried by the third absorbent material to a third portion of the patient's tissue; and
retracting the shielding rod through the hollow casing away from the opening.

11. The method of claim 9, further comprising creating an incision in the eye of the patient; and wherein repositioning the hollow casing includes pivoting the hollow casing at the incision to direct the opening of the hollow casing toward the second portion of the patient's tissue.

12. The method of claim 7, wherein further comprising;

forming a void in fibroblasts positioned in the subconjunctival space of the patient's tissue;

marking the first portion of the patient's tissue to indicate a target region for the substance to be applied;

wherein the target region is defined along a boundary of the void.

13. The method of claim 7, further comprising:

selecting a desired surface area of the first absorbent material to be exposed to the first portion of the patient's tissue based on at least the concentration of the substance and the time the first absorbent material is to be applied to the patient's tissue.

14. The method of claim 13, further comprising:

adjusting the surface area of the first absorbent material to be exposed to the first portion of the patient's tissue based on the desired surface area;

wherein adjusting the surface area of the first absorbent material includes moving a bottom portion of the shield relative to a main body of the shielding rod.

15. A method of operating an applicator assembly comprising:

inserting a first shielding rod having a first absorbent material coupled thereto into a hollow casing;

advancing the first shielding rod through the hollow casing toward an opening of the hollow casing;

applying a substance carried by the first absorbent material to a first portion of patient's tissue;

retracting the first shielding rod through the hollow casing away from the opening.

16. The method of claim 15, wherein the first portion of patient's tissue is a target region to which the drug is to be applied; and wherein applying a substance carried by the first absorbent material to a first portion of patient's tissue includes:

contacting the target region with the first absorbent material, and contacting a non-targeted region, to which the substance is not to be applied, with a shield of the shielding rod positioned adjacent the first absorbent material.

17. The method of claim 15, further comprising:

repositioning the hollow casing;

inserting a second shielding rod into the hollow casing with a second absorbent material attached to the second shielding rod;

advancing the second shielding rod through the hollow casing toward the opening of the hollow casing;

applying a substance carried by the second absorbent material to a second portion of the patient's tissue; and retracting the second shielding rod through the hollow casing away from the opening.

18. The method of claim 17, further comprising creating an incision in the eye of the patient; and wherein repositioning the hollow casing includes pivoting the hollow casing at the incision to direct the opening of the hollow casing toward the second portion of the patient's tissue.

19. The method of claim 15, further comprising:

selecting a desired surface area of the first absorbent material to be exposed to the first portion of the patient's tissue based on at least the concentration of the substance and the time the absorbent material is to be applied to the patient's tissue.

20. The method of claim 19, further comprising:

adjusting the surface area of the first absorbent material to be exposed to the first portion of the patient's tissue based on the desired surface area; and wherein adjusting the surface area of the first absorbent material to be exposed includes moving a bottom portion of the shield.

* * * * *